(12) United States Patent
Giftakis et al.

(10) Patent No.: US 12,280,261 B2
(45) Date of Patent: Apr. 22, 2025

(54) MEDICAL DEVICE PATIENT ALERT USING HOUSING STIMULATION BASED ON SENSED EVENT

(71) Applicant: Medtronic, Inc., Minneapolis, MN (US)

(72) Inventors: Jonathon E. Giftakis, Maple Grove, MN (US); Scott R. Stanslaski, Shoreview, MN (US); William C. Harding, Chandler, AZ (US); Ryan Gertenbach, Chandler, AZ (US); Brian L. Bechard, St. Paul, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 17/645,682

(22) Filed: Dec. 22, 2021

(65) Prior Publication Data

US 2022/0266041 A1 Aug. 25, 2022

Related U.S. Application Data

(60) Provisional application No. 63/152,930, filed on Feb. 24, 2021.

(51) Int. Cl.
*A61N 1/36* (2006.01)
*A61N 1/02* (2006.01)
(Continued)

(52) U.S. Cl.
CPC ......... *A61N 1/37258* (2013.01); *A61N 1/025* (2013.01); *A61N 1/0551* (2013.01); *A61N 1/08* (2013.01); *A61N 1/36175* (2013.01)

(58) Field of Classification Search
None
See application file for complete search history.

(56) References Cited

U.S. PATENT DOCUMENTS

| 4,140,131 A | 2/1979 | Dutcher et al. |
| 5,304,206 A | 4/1994 | Baker, Jr. et al. |

(Continued)

FOREIGN PATENT DOCUMENTS

| CN | 102451520 A | 5/2012 | |
| CN | 112351813 A | * 2/2021 | ............... A61B 5/24 |

OTHER PUBLICATIONS

CN112351813-A Translation (Year: 2021).*

(Continued)

*Primary Examiner* — Erica S Lee
(74) *Attorney, Agent, or Firm* — Shumaker & Sieffert, P.A.

(57) ABSTRACT

An implantable medical device that includes a memory, stimulation circuitry configured to deliver electrical stimulation to a patient, and processing circuitry operably coupled to the memory. The processing circuitry is configured to: control the stimulation circuitry to output electrical stimulation therapy to a patient via a first electrode combination and control the stimulation circuitry to output a notification stimulation via a second electrode combination and interleaved with the electrical stimulation therapy. The notification stimulation may include an intensity above a perception level of the patient, and the second electrode combination may include an electrode disposed at an implant site of the implantable medical device.

21 Claims, 7 Drawing Sheets

(51) Int. Cl.
*A61N 1/05* (2006.01)
*A61N 1/08* (2006.01)
*A61N 1/372* (2006.01)

(56) References Cited

U.S. PATENT DOCUMENTS

| | | | |
|---|---|---|---|
| 6,080,187 | A | 6/2000 | Alt et al. |
| 7,574,259 | B1 | 8/2009 | Pei et al. |
| 7,606,618 | B1 | 10/2009 | Bornzin et al. |
| 7,672,716 | B1 | 3/2010 | Koh |
| 7,734,345 | B2 | 6/2010 | Cinbis |
| 7,774,056 | B2 | 8/2010 | Torgerson |
| 7,962,210 | B2 | 6/2011 | Daum et al. |
| 7,996,084 | B2 | 8/2011 | Stylos et al. |
| 8,121,691 | B2 | 2/2012 | Gerber et al. |
| 8,145,320 | B2 | 3/2012 | Corndorf et al. |
| 8,301,231 | B2 | 10/2012 | Fischell et al. |
| 8,380,303 | B2 | 2/2013 | Rosenberg et al. |
| 8,457,725 | B1 | 6/2013 | Fischell et al. |
| 8,591,455 | B2 | 11/2013 | Mensinger et al. |
| 8,760,284 | B2 | 6/2014 | Petersen et al. |
| 8,897,879 | B2 | 11/2014 | Karamanoglu et al. |
| 9,185,489 | B2 | 11/2015 | Gerber et al. |
| 9,186,509 | B2 | 11/2015 | Nelson et al. |
| 10,543,359 | B2 | 1/2020 | Giftakis et al. |
| 10,665,080 | B2 | 5/2020 | Lee |
| 10,805,742 | B2 | 10/2020 | Van Gerwen |
| 10,869,808 | B2 | 12/2020 | Fung et al. |
| 2002/0099412 | A1 | 7/2002 | Fischell et al. |
| 2007/0255339 | A1* | 11/2007 | Torgerson ............ A61N 1/0529 607/45 |
| 2007/0255347 | A1 | 11/2007 | Torgerson et al. |
| 2008/0046016 | A1 | 2/2008 | Ben-David et al. |
| 2009/0228073 | A1 | 9/2009 | Scholten |
| 2011/0082376 | A1 | 4/2011 | Huelskamp |
| 2011/0208455 | A1 | 8/2011 | Tobacman |
| 2012/0179015 | A1 | 7/2012 | Mann et al. |
| 2012/0194341 | A1 | 8/2012 | Peichel et al. |
| 2013/0030497 | A1 | 1/2013 | Karamanoglu |
| 2014/0213926 | A1 | 7/2014 | Vaidyanathan |
| 2014/0350636 | A1 | 11/2014 | King |
| 2015/0297901 | A1 | 10/2015 | Kockx |
| 2016/0243373 | A1 | 8/2016 | Kalgren |
| 2017/0360381 | A1 | 12/2017 | McGarraugh |
| 2018/0001096 | A1* | 1/2018 | Faltys .................. A61N 1/3787 |
| 2018/0093101 | A1* | 4/2018 | Maile .................. A61N 1/37217 |
| 2019/0001135 | A1 | 1/2019 | Yoo et al. |
| 2019/0386498 | A1 | 12/2019 | Higgins |
| 2020/0054292 | A1 | 2/2020 | Govari |
| 2020/0113515 | A1* | 4/2020 | O'Connor .......... A61B 5/02055 |
| 2020/0139139 | A1 | 5/2020 | Crawford |
| 2020/0228905 | A1 | 7/2020 | Dundas |
| 2020/0324126 | A1 | 10/2020 | Winstrom |
| 2020/0381086 | A1 | 12/2020 | Atreja et al. |
| 2020/0403717 | A1 | 12/2020 | Fishler et al. |

OTHER PUBLICATIONS

Devinsky et al., "Sudden unexpected death in epilepsy in patients treated with brain-responsive neurostimulation," Epilepsia, vol. 59, Dec. 11, 2017, pp. 555-561.

Holz et al., "Implanted User Interfaces," CHI '12, Proceedings of the SIGCHI Conference on Human Factors in Computing Systems, May 2012, pp. 503-512.

The Week Staff, "The implant that alerts you before a heart attack", TheWeek.com, Apr. 19, 2012, 7 pp.

U.S. Appl. No. 17/645,661, filed Dec. 22, 2021, naming inventors Giftakis et al.

U.S. Appl. No. 17/645,669, filed Dec. 22, 2021, naming inventors Giftakis et al.

Office Action from U.S. Appl. No. 17/645,661 dated Jul. 20, 2023, 24 pp.

Final Office Action from U.S. Appl. No. 17/645,661 dated Dec. 8, 2023, 13 pp.

Response to Office Action dated Jul. 20, 2023 from U.S. Appl. No. 17/645,661, filed Oct. 19, 2023, 16 pp.

Advisory Action from U.S. Appl. No. 17/645,661 dated Feb. 15, 2024, 3 pp.

Office Action from U.S. Appl. No. 17/645,669 dated Feb. 28, 2024, 15 pp.

Response to Final Office Action dated Dec. 8, 2023 from U.S. Appl. No. 17/645,661, filed Feb. 8, 2024, 14 pp.

Office Action from U.S. Appl. No. 17/645,661 dated May 1, 2024, 7 pp.

Response to Office Action from U.S. Appl. No. 17/645,669, filed May 28, 2024, 17 pp.

Response to Final Office Action dated May 1, 2024 from U.S. Appl. No. 17/645,661, filed Jul. 25, 2024, 11 pp.

Final Office Action from U.S. Appl. No. 17/645,669 dated Sep. 6, 2024, 15 pp.

Office Action from U.S. Appl. No. 17/645,661 dated Oct. 15, 2024, 25 pp.

* cited by examiner

MEDICAL DEVICE PATIENT ALERT USING HOUSING STIMULATION BASED ON SENSED EVENT

This Application claims the benefit of U.S. Provisional Patent Application 63/152,930, filed 24 Feb. 2021, the entire content of which is incorporated herein by reference.

TECHNICAL FIELD

This disclosure generally relates to medical devices, and more specifically, communication systems and techniques for medical devices.

BACKGROUND

Medical devices may be external or implanted, and may be used to deliver therapy, such as electrical stimulation therapy or other therapies, to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS). In some examples, a user may receive information related to the operation of the medical device from an external device in communication with the medical device.

SUMMARY

In general, the disclosure is describing systems, devices, and techniques for outputting an alert to a subject in one or more of several different alert modes. Some examples of alert modes may include an audible alert, a signal to an external device, an alert that the patient can feel such as vibration or paresthesia, a signal sent to another part of the patient's body through a body network pathway, changes in delivery of electrical stimulation therapy that may be detectable by the patient, and similar alert modes. In the example of an implantable medical device, the signal sent to another part of the patient's body may be sent to a second implantable medical device, to the patient's auditory nerve to provide an apparent audible alert, as well as other locations. In some examples, the medical device may output the alert signal to communicate a system status or respond to a patient input to the medical device. For example, the alert signal may acknowledge a series of taps provided by the user on the medical device that requests a change to the operation of the medical device and/or confirm that the operational change has been made. In some examples, the medical device may communicate with an external device that includes a user interface. The external device may be configured to assign alert modalities to a particular detected condition, enable or disable alert signals, cause the medical device to output a specific alert for patient training or confirmation, as well as receive and display alerts from the medical device.

In one example, this disclosure describes a medical system comprising a memory configured to store instructions for selecting an alert mode from a plurality of alert modes; and processing circuitry configured to: determine that a condition occurred, the condition associated with at least one of a patient or an implantable medical device; responsive to determining that the condition occurred, select the alert mode from the plurality of alert modes based on the condition, and the instructions; and responsive to selecting the alert mode, output, in the selected alert mode, an alert that indicates the condition occurred.

In another example, this disclosure describes a method comprising determining, by processing circuitry operatively coupled to a memory, that a condition occurred, the condition associated with at least one of a patient or an implantable medical device; responsive to determining that the condition occurred, accessing, by the processing circuitry, instructions stored at the memory for selecting an alert mode from a plurality of alert modes, and selecting the alert mode from the plurality of alert modes based on the condition; responsive to selecting the alert mode, outputting, in the selected alert mode, an alert that indicates the condition occurred.

In another example, this disclosure describes a system that includes an external computing device comprising a user interface; an implantable medical device includes a memory configured to store instructions for selecting an alert mode from a plurality of alert modes; and processing circuitry configured to: determine that a condition occurred, the condition associated with at least one of a patient or the implantable medical device; responsive to determining that the condition occurred, select the alert mode from the plurality of alert modes based on the condition and the instructions; and responsive to selecting the alert mode, output, in the selected alert mode, an alert that indicates the condition occurred.

In one example, this disclosure describes a system that includes a movement sensor configured to be implanted within a patient and generate a movement signal; and processing circuitry configured to be implanted within the patient and configured to: receive the movement signal from the movement sensor; determine that the movement signal is representative of a communication from the patient; responsive to determining that the movement signal is representative of the communication: output an alert to the patient that is associated with the communication; and perform an action requested by the communication.

In another example, this disclosure describes a method comprising receiving, by processing circuitry configured to be implanted within a patient, a movement signal from a movement sensor, wherein the movement sensor is also configured to be implanted within the patient; determining, by processing circuitry, that the movement signal is representative of a communication from the patient; responsive to determining that the movement signal is representative of the communication: causing, by the processing circuitry, an alert to be output to the patient that is associated with the communication; and performing an action requested by the communication.

In another example, this disclosure describes a computer-readable medium with instructions for causing a programmable processor of an implantable medical device to: receive a movement signal from a movement sensor, wherein the implantable medical device comprises the movement sensor; determine that the movement signal is representative of a communication from the patient; responsive to determining that the movement signal is representative of the communication: cause an alert to be output to the patient that is associated with the communication; and perform an action requested by the communication In one example, this disclosure describes an implantable medical device that includes a memory; stimulation circuitry configured to deliver electrical stimulation to a patient; and processing circuitry operably coupled to the memory and configured to: control the stimulation circuitry to output electrical stimulation therapy to a patient via a first electrode combination; and control the stimulation circuitry to output a notification stimulation via a second electrode combination and interleaved with the electrical stimulation therapy, wherein the notification stimulation comprises an intensity above a perception level of the patient, and wherein the second electrode combination comprises an electrode disposed at an implant site of the implantable medical device.

In another example, this disclosure describes a method comprising controlling, by processing circuitry operably coupled to a memory, stimulation circuitry configured to output electrical stimulation therapy to a patient; and controlling, by the processing circuitry, the stimulation circuitry to output the electrical stimulation therapy to a patient via a first electrode combination; and controlling, by the processing circuitry, the stimulation circuitry to output a notification stimulation interleaved with the electrical stimulation therapy wherein the notification stimulation comprises an intensity above a perception level of the patient, and wherein the second electrode combination comprises an electrode disposed at an implant site of the implantable medical device.

In another example, this disclosure describes a computer-readable medium with instructions for causing a programmable processor of a medical device to control stimulation circuitry, wherein the stimulation circuitry is configured to: output electrical stimulation therapy to a patient; and output a notification stimulation interleaved with the electrical stimulation therapy wherein the notification stimulation comprises a housing stimulation at an implant site of the implantable medical device above a perception level of the patient.

The details of one or more examples of the disclosure are set forth in the accompanying drawings and the description below. Other features, objects, and advantages of the disclosure will be apparent from the description and drawings, and from the claims.

DETAILED DESCRIPTION

Patients that carry medical devices for extended periods, either implantable, or wearable medical devices, may benefit from notifications from the device. Notifications may be useful to alert the patient, or the patient's medical provider, of a detected physiological condition, a detected device condition, such as a battery charge level, and so on. The techniques of this disclosure describe outputting an alert in one or more of several different alert modes. Examples of alert modes may include an audible alert, a signal to an external device, an alert that the patient can feel such as vibration or paresthesia, a signal sent to another part of the patient's body through a body network pathway, changes in delivery of electrical stimulation therapy that may be detectable by the patient, and similar alert modes.

For an implantable medical device, the signal through the body network pathway may be received by the patient's auditory nerve to provide an apparent audible alert. In some examples, the medical device may output the alert signal to communicate a system status or respond to a patient input to the medical device. For example, the alert signal may acknowledge a series of taps provided by the user on the medical device that requests a change to the operation of the medical device and/or confirm that the operational change has been made. In some examples, the medical device may communicate with an external device that includes a user interface. The external device may be configured to assign alert modalities to a particular detected condition, enable or disable alert signals, cause the medical device to output a specific alert for patient training or confirmation, as well as receive and display alerts from the medical device.

The techniques of this disclosure may provide advantages over other notification techniques. For example, some alert modes for notifications may not require additional hardware from the hardware already included in a medical device. Additional hardware such as a vibrator or beeper may be added to a device but may make the medical device more expensive and/or larger. Some very small implantable medical devices may not be able to accommodate added hardware. Devices of this disclosure may configure alert modes based on the patient ability. For example, a user may have limited hearing acuity, tactile sensitivity, visual acuity and so on. For a patient with difficulty hearing, a device of this disclosure may select an alert mode that does not depend on an audible alert. Other examples of alert modes may not rely on the patient managing an external peripheral device, e.g., a patient programmer or other type of external device, which may simplify the notification process compared to other techniques that require an external display.

Figure 1:
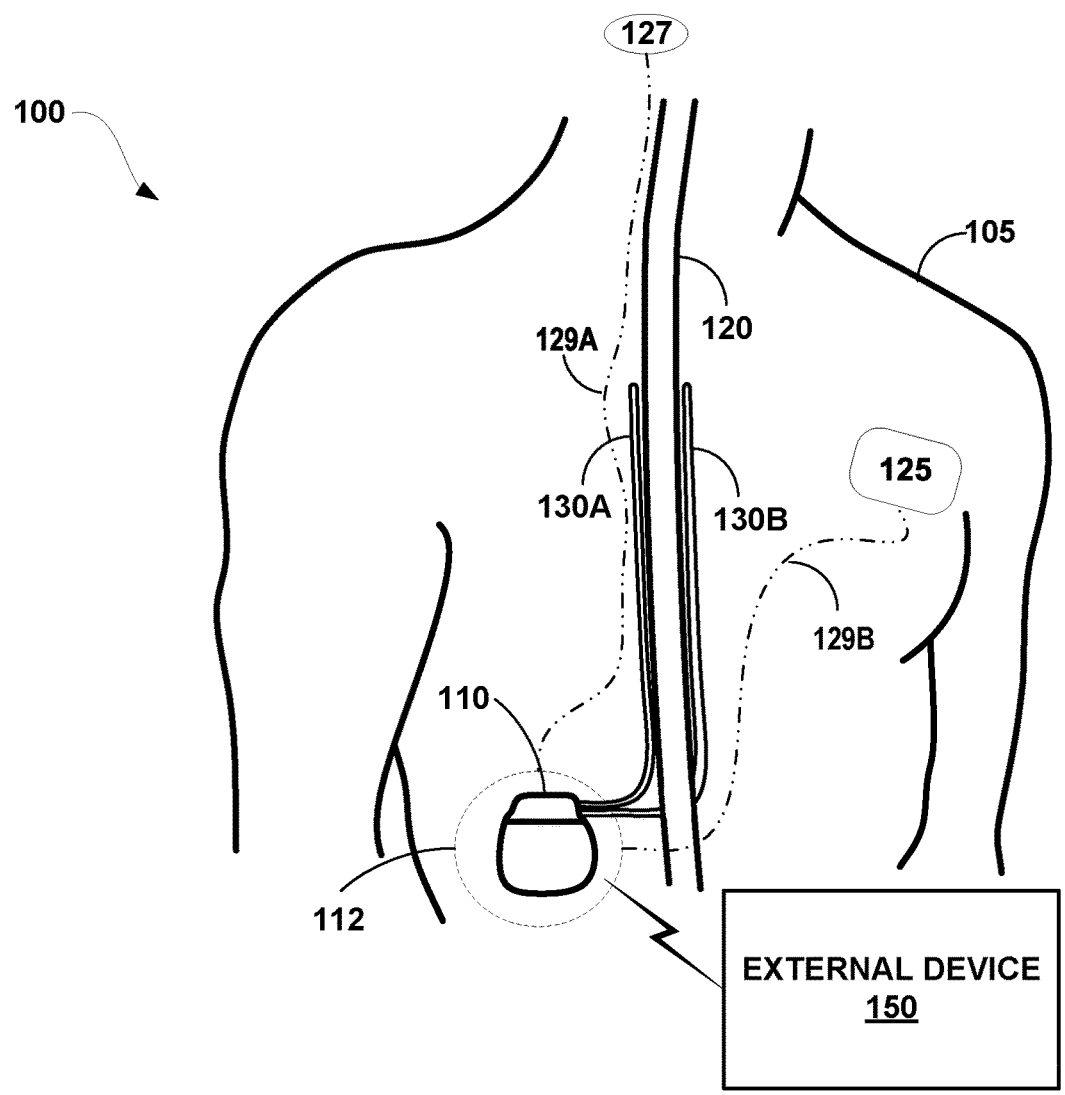
FIG. 1 is a conceptual diagram illustrating a medical system configured to deliver notifications with a variety of alert modes according to one or more techniques of this disclosure.

FIG. 1 is a conceptual diagram illustrating a medical system configured to deliver notifications with a variety of alert modes according to one or more techniques of this disclosure. System 100, in the example of FIG. 1 includes a first implantable medical device IMD 110, leads 130A and 130B, which may include one or more electrodes (not shown in FIG. 1), and a second medical device 125 in some examples, which may be implantable or wearable.

In the example of FIG. 1, leads 130A and 130B (collectively leads 130) are disposed within patient 105, e.g., implanted within patient 105. Leads 130 may tunnel through tissue of patient 105 from adjacent to spinal cord 120 to subcutaneous tissue pocket 112 or other internal location where IMD 110 is disposed. In other examples, electrodes of leads 130 may be implanted adjacent to a tibial nerve of patient 105, or some other location (not shown in FIG. 1).

In some examples, leads 130 may be a single lead, and may include a lead extension or other segments that may aid in implantation or positioning of leads 130 (not shown in FIG. 1). In addition, a proximal end of lead 314 may include a connector (not shown) that electrically couples to a header of IMD 110. Although shown disposed along spinal cord, leads 130 may be directed to the spinal cord and/or other locations, e.g., the tibial region, within brain tissue, e.g., for deep brain stimulation (DBS), cardiac tissue, or other locations within patient 105.

The housing of IMD 110 may be constructed of any polymer, metal, ceramic, or composite material sufficient to house the components of IMD 110. IMD 110 may be constructed with a biocompatible housing, such as titanium or stainless steel, ceramic, or a polymeric material such as silicone, polysulfone, or polyurethane, and surgically implanted at a site in patient 105 near the pelvis, abdomen, tibia, or buttocks. The housing of IMD 110 may be configured to provide a hermetic seal to protect components housed within IMD 110. The housing of IMD 110 may also be referred to as a can or case for IMD 110 in this disclosure. In some examples, all or a portion of the housing of IMD 110 may be electrically conductive in order to provide a portion of a path for electrical current used to deliver a stimulus to patient 100.

IMD 110 and external device 150 may be communicatively linked via a communication and/or power link. As described herein, information may be transmitted between IMD 110 and external device 150 using one or more wireless communication techniques. Examples of communication techniques may include, for example, low frequency or RF telemetry. In some examples, external device 150 may be referred to as a clinician programmer or patient programmer because it is configured to program one or more operations of IMD 110 and IMD 125. In some examples external device 150 may include a charging device configured to recharge a power source of IMD 110 and IMD 125. In some examples external device 150 may couple to a wand, headset, or similar device (not shown in FIG. 1) that may include one or more antennae and is placed closed to IMD 110 during the charging or communication process. External device 150 may include one or more input and/or output devices that enable a user, such as a clinician or patient 105, to interact with a user interface of external device 150 to program IMD 110, and/or to otherwise interface with system 100. In some examples, a user interface may include a display screen configured to display information, such as text and/or graphical information, to the user. In some examples, user interface includes an input device, such as a touch screen, buttons, knobs and so on, that allows a user to provide inputs to the external device 150 and thus to system 100.

In some examples, IMD 110 may include a memory (not shown in FIG. 1) configured to store instructions for selecting an alert mode from a plurality of alert modes. IMD 110 may also include processing circuitry connected to the memory. The processing circuitry may be configured to determine whether the processing circuitry should send a notification, for example, to patient 105, to a clinician or other caregiver, or to a health tracking system for patient 105. In some examples, the processing circuitry may determine that a condition occurred that may be associated with at least one of patient 105 or implantable medical device 110.

A condition may be associated with a patient or IMD 110. Some examples of conditions associated with patient 105 (e.g., a patient condition that may include a physiological condition), may include a consciousness level of the patient, a pain level, an activity level, a posture, a gait freeze, a cardiac arrhythmia, a seizure, an incontinence event, a bladder filling event, epileptiform activity, a blood sugar level crossing a threshold, a local field potential (LFP) crossing a threshold, or any other condition that may be representative of the patient. Some conditions may be reflective of symptoms of a disease or injury, and some conditions may be caused by effective therapy. Examples of patient consciousness level may include awake, sleeping, coma and so on. Other examples of patient condition may include a missed medication dosage, which may be sensed by IMD 110 or by expiration of a timer. Examples of conditions associated with a medical device (e.g., IMD 110) may include therapy is active, therapy is inactive, a low battery level, recharging wand position indicator, recharging complete, a breakage or other connection issue with one or more of leads 130, a communication error, a memory error, or any other device issue or status.

The processing circuitry, which may be part of IMD 110 or another device, may be configured to select the alert mode from the plurality of alert modes based on the detected condition and the instructions stored at the memory. The instructions may cause the processing circuitry to select a particular alert mode based on the type of condition. For example, the instructions may associate a seizure with a first alert mode and a battery level indicator with a second, and different, alert mode. Based on the instructions the processing circuitry may change alert mode or change the alert intensity (e.g., increase volume, faster pulse repetition rate, etc.) for second or third repeated alert. After selecting the alert mode, the processing circuitry may cause other circuitry to output, in the selected alert mode, an alert, e.g., a notification that indicates the condition occurred.

In some examples, the processing circuitry may be programmed to select an alert mode depending on the ability of patient 105 to detect one or more alert modes of the plurality of alert modes. For example, because of the hearing acuity, or lack thereof, of patient 105, the patient may have difficulty hearing tones at certain audio frequencies. The processing circuitry may be programmed to select audio frequencies within the patient's hearing range, or in some examples, to select a non-audio alert mode. In some examples, patient 105 may have diminished or heightened tactile sensitivity. For a patient unable to detect vibrations of either an implanted device, or an external wearable device, the processing circuitry may be programmed to select an alert mode that does not include vibration. In some examples, patient 105 and/or a clinician may provide input identifying any alert modes that should be excluded from selection and/or alert modes that should be used for patient 105.

In some examples, IMD 110 may directly receive input from patient 105. The processing circuitry, e.g., within IMD 110 or external device 150, may receive a movement signal from the movement sensor and determine that the movement signal is representative of the communication from patient 105 (or another user). The movement sensor may be located within the housing of IMD 110, IMD 125, or otherwise implanted or available to patient 105. An example of a movement sensor may include an accelerometer. The communication may be in the form of one or more taps (e.g., through the skin) on a housing of the implantable medical device that houses the movement sensor. The movement sensor, or the processing circuitry by way of analysis of output from the movement sensor, may detect the one or more taps as one or more movements in a single direction exceeding a threshold. In other words, the movement sensor may sense a movement in a single direction as a tap, and determine that the tapping is a communication, only when the tapping causes a movement abrupt enough, e.g., movement within a time duration and with a high enough magnitude to exceed a threshold.

Responsive to determining that the movement signal is representative of the communication, the processing circuitry, e.g., of IMD 110 or external device 150, may output an alert to the patient that is associated with the communication, e.g., to acknowledge the communication. In addition, the processing circuitry may perform an action requested by the communication. In the example in which IMD 110 includes a battery, the processing circuitry may interpret the tapping as a request to receive a status of the battery discharge level. The processing circuitry may be configured to perform the requested action by obtaining the discharge level of the battery and output the alert in a selected alert mode that indicates the discharge level of the battery.

In some examples, the processing circuitry may determine a pattern defined by the of taps based on the received movement signal. Different patterns may be associated with requests from the user for IMD 110 to perform different actions. In one example, the pattern may be a predetermined number of taps within a predetermined duration, e.g., four taps within three seconds. In other examples, the pattern may be a predetermined frequency of taps, e.g., a rapid series of taps or a slow series of taps. In other words, the predetermined frequency may be a predetermined period of time between at least two taps of the series of taps. That is, a "rapid" series of taps may have a short period of time, or duration between taps when compared to a "slow" series of taps with a longer period of time between taps.

In other examples, wherein the series of taps may include a first tap, a second tap, and a third tap. The pattern may be defined by a first period of time between the first tap and the second tap and a second period of time between the second tap and the third tap, in which the first period is longer than the second period. In other examples, the pattern may be defined by a first tap at a first magnitude and a second tap at a second magnitude, in which the first magnitude is greater than the second magnitude.

In other examples, the communication may include patient 105 causing one or more jiggle movements of the housing of IMD 110, or a separate movement sensor. The movement sensor may be configured to detect the one or more jiggle movements as one or more movements in opposite directions exceeding a threshold. In this disclosure, a movement may be also be a velocity, acceleration, change in accelerations, or a fluctuation frequency above a threshold and so on. The processing circuitry may determine the communication based on the pattern of movements, and select the action to perform, based on the determined communication.

In some examples, an alert mode may include an audible notification, such as a tone, series of tones or similar. IMD 110, or external device 150, may include a speaker, or some similar component, that may generate the tone, a spoken alert, or some other type of audible alert. In other examples, a device of system 100 may include a visible indicator, such as a view screen, light source or similar. In other examples, IMD 110, or external device 150 may include a vibration generator to cause a vibration perceptible to patient 105.

One or more alert modes may include notifications that indirectly reach patient 105, a caregiver, or an external server, e.g., via communication to external device 150. Some examples of alert modes may include notifications via Bluetooth®, Wi-Fi, mobile phone, e.g., text message, to a smart speaker, e.g., Amazon Alexa, Google Home and so on, a fitness tracker and other similar external devices. In some examples, IMD 110 be programmed to select an alert mode that sends a notification via a biological pathway to a fitness tracker that may sound an audible alert, a vibration, display a message or some similar alert mode to notify the patient, e.g., of a condition of IMD 110 or of the patient. In other examples, IMD 110 may output a wireless signal to a hearing aid to provide an audible alert to patient 105.

In some examples, alert modes for notifications may not require additional hardware from the hardware already included in IMD 110, which may provide advantages over hardware such as a vibrator or beeper that would otherwise need to be added as part of IMD 110. Additional hardware may make the medical device more expensive and/or larger. Other examples of alert modes may not rely on the patient managing an external peripheral device, e.g., a patient programmer or other type of external device.

Some example alert modes may include communications distribution throughout a biological environment, e.g., the human body of patient 105. Some communication pathways e.g., body network pathways 129A and 129B, may use specific conductive tissue, such as muscular arteries, where that tissue is spread throughout the body, more conductive than other tissue, and such that the tissue could be used as a low power or communications bus (or conduit) for distribution to and from target devices, sensors, and other biological components e.g., heart, visual and auditory cortex. In this manner IMD 110, IMD 125 and other non-implanted devices may enable the patient's tissue, nervous system, muscles, and vascular system to function as a distribution conduit. In other words, in some examples, the system may use patient's body tissue to transfer power from a power source to a medical device, either or both of which may be implanted.

In some examples, specific neurological pathways may move signals from one point to another, such as through the brain stem, the reticular formation, i.e., the region in the brain stem consisting of hundreds of small neural networks, to the thalamus, and ending in one or more sensory area located in the cerebral cortex, i.e., an outer layer of the cerebrum of patient 105. In some examples, the communication distribution may include a leadless, lead-based, and possibly wireless techniques for using biological components as a platform (e.g., a conduit) for moving device and/or sensor signals around the body. In some examples, system 100 may include various forms of in-body repeaters, extenders, or other nodes to boost power, communication signals, reconstitute fragmented data, and bridge areas that may present a barrier to normal electrical signals, such as by using low power radio frequency (RF) or other wireless techniques. In some examples, system 100 may include implanted sensors located deeper within the body where traditional signals such as RF may have had difficulty penetrating.

As one example, a body network pathway, such as pathway 129A, may bypass other methods of processing auditory signals, e.g., with a tone generator, and enable the injection of sounds directly into a patient's nervous system. That is, instead of a system that imitates a patient's ears and the associated components to process auditory signals, such as a cochlear implant, an alert mode of this disclosure may include techniques in which auditory nerve 127, or other brain tissue of patient 105, receives the signal through the body network pathway and the received signal may cause auditory nerve 127 to provide an apparent audible alert to patient 105. In other words, to transmit a "sound" within the body of patient 105, system 100 may function such that the patient's auditory system will interpret signals as sound, provided that the signals make their way through the nervous system, into the brain stem, and then into the auditory cortex.

In a similar manner, the medical device may transmit a visual signal to brain tissue of the patient for a notification. The visual signal may be in the form of an image, a flash of color, or some similar notification.

In other examples, first implantable medical device 110 may send a signal to second medical device 125 via pathway 129B, e.g., device-to-device (D2D) communication. Second medical device 125 may receive the signal through the body network pathway 129B and provides the notification to the patient in the selected alert mode. In some examples, a network of biological pathways may be referred to as a body mesh. In some examples, the signals output to the body network pathway may be configured such that the transmitted signals may only be received by the targeted device. In this manner, the transmitted signals may avoid interference by other biological signals or by signals from other devices.

For other example alert modes, processing circuitry may control stimulation circuitry of IMD 110 to temporarily adjust the therapy or add to the electrical stimulation therapy such that the patient is aware of the change. In other words, IMD 110 or IMD 125 may output a notification stimulation with an intensity above a perception level of the patient. In some examples, the notification stimulation may be interleaved with the electrical stimulation therapy. In other examples, other alert modes may include a modification to stimulation therapy delivered by IMD 110. A modification to the stimulation therapy may include one or more of: withhold the stimulation therapy for a predetermined duration, change intensity of the stimulation therapy for the predetermined duration, modify the stimulation therapy in a predetermined pattern, and similar modifications.

As one specific example, processing circuitry of IMD 110 may select an alert mode that provides the notification stimulation, while still providing electrical stimulation therapy for the medical condition of patient 105, e.g., chronic pain, Parkinson's disease, incontinence and so on. The notification stimulation may include an additional pulse or small group of pulses are added to the therapy that momentarily alerts the patient, for example, that the battery level has crossed a threshold. The notification stimulation can be delivered at the regular therapeutic location via one or more leads or at a different location from therapy, such as pocket 112. The alert mode of the pulse or set of pulses may deliver a short and mild stimulation sensation to the patient, for example. In some cases, the notification stimulation may be perceived as paresthesia, but in other examples the notification stimulation may be a stimulus that is noticeable but not painful. In other examples, the processing circuitry may momentarily pause therapy so that the side effects from a short loss of therapy may be observed by the patient. For example, a tremor patient may see that that their tremor returns for a given amount of time and then the therapy turns back on to again provide the therapy. For a patient with a dual hemisphere lead system, the processing circuitry may alter therapy to one hemisphere and have side effects appear for a short time (tremor on one side for example), without putting the patient at any risk of any serious recurrence of conditions. Some DBS patients may notice when electrical stimulation therapy is turned on and off, not by the return of side effects, but the patients may sense or momentarily feel something different when the stimulation is ramping down or up for DBS. The alert mode may include a notification stimulation that may ramp down followed by a ramp up, with a ramp rate chosen to allow this sensation to notify the patient while minimizing any interruption in therapy.

For other example alert modes, processing circuitry of IMD 110 may control the stimulation circuitry to output normal electrical stimulation therapy to patient 105 via a first electrode combination on either or both of leads 130A or 130B. The processing circuitry may further control the stimulation circuitry to output the notification stimulation above the perception level of the patient via a second electrode combination and interleaved with the electrical stimulation therapy delivered via electrodes of leads 130. The second electrode combination may include an electrode disposed at an implant site of IMD 110. In some examples, the second electrode combination may include the housing of IMD 110. For example, the housing of IMD 110 may be a conductive material such as a titanium alloy, that may connect to the electrical stimulation circuitry of IMD 110. In other examples an electrode integrated with the housing of the implantable medical device but electrically isolated from the housing may act as part of the second electrode combination to deliver the notification stimulation. Such an electrode may include an electrode in or attached to the header, e.g., an indifferent electrode, or an electrode attached to the housing (also called the case) and separated from the housing by an insulative material. In some examples the housing, the indifferent electrode or an electrode on a lead implanted proximal to the implant site may act as a cathode to deliver the notification stimulation. The second electrode combination may also include one or more electrodes implanted separate from the implant site and configured to act as one or more anodes for the notification stimulation.

The processing circuitry may cause the electrical stimulation circuitry to cause sensation above a perception threshold of the patient between the housing of IMD 110 and tissue of the patient at an implant site of the implantable medical device. In some examples, the processing circuitry may control the stimulation circuitry to deliver the notification stimulation with a pattern of pulses detectable by the patient at the implant site. The stimulation circuitry may deliver the pattern of pulses at a predetermined pulse repetition rate, for example, at a slower pulse repetition rate for one condition, e.g., mild epileptiform activity, and a faster rate repetition rate to indicate a seizure may be imminent. In other examples, the pattern may include pulses at different times. For example, a first period of time between a first pulse and a second pulse and a second period of time between the second pulse and a third pulse, in which the first period is longer than the second period. A notification stimulation pattern may be representative or well-known musical pattens (e.g., the "shave and a haircut" rhythm), or another recognizable pattern. In some examples, patient 105 or the clinician may select a desired pattern via external device 150. The pattern may also repeat more than once. In other examples, the pulses detectable by the patient may include a gradually increasing magnitude for each pulse of the plurality of pulses over a predetermined duration. In other examples, the pulses detectable by the patient may include a first pulse at a first magnitude and a second pulse at a second magnitude, in which, for example, the first magnitude is greater than the second magnitude.

Leads 130 may carry one or more electrodes that are placed adjacent to the target tissue, e.g., spinal cord for spinal cord stimulation (SCS) therapy. One or more electrodes may be disposed at a distal tip of leads 130 and/or at other positions at intermediate points along leads 130. The electrodes of lead 314 may transfer electrical stimulation to tissue of patient 105. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar, or multipolar electrode configurations for therapy.

Figure 2:
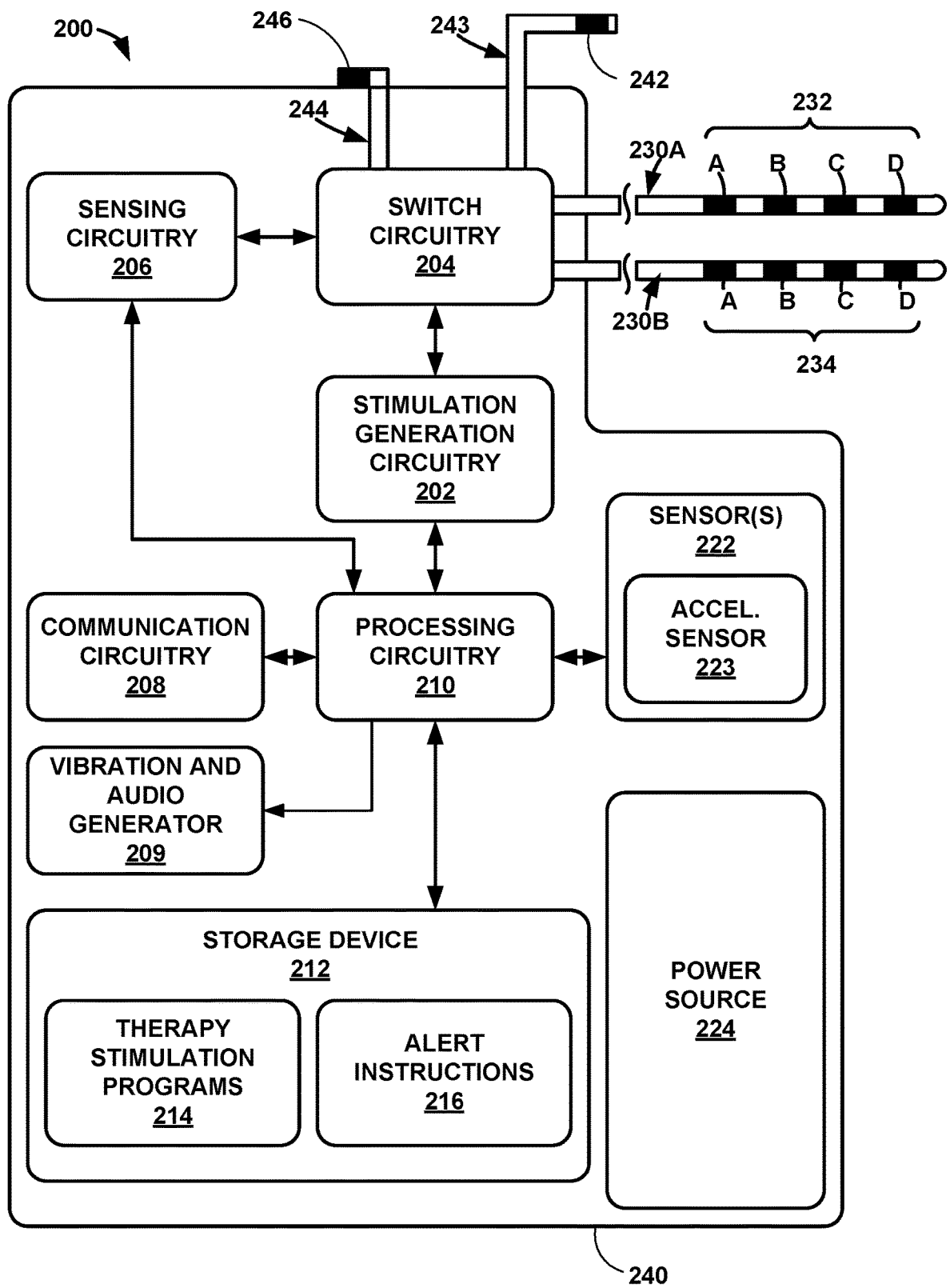
FIG. 2 is a block diagram illustrating a medical device configured to deliver electrical stimulation therapy and notifications according to one or more techniques of this disclosure.

FIG. 2 is a block diagram illustrating an example configuration of components of IMD 200, in accordance with one or more techniques of this disclosure. IMD 200 may be an example of IMD 110 and IMD 125 of FIG. 1. In the example shown in FIG. 2, IMD 200 includes stimulation generation circuitry 202, switch circuitry 204, sensing circuitry 26, Communication circuitry 208, processing circuitry 210, storage device 212, sensor(s) 222, and power source 224. As seen in FIG. 2, sensor(s) 222 include acceleration sensor 223.

In the example shown in FIG. 2, storage device 212 stores therapy stimulation programs 214 and alert instructions 216 in separate memories within storage device 212 or separate areas within storage device 212. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Alert instructions 216 may assign a particular condition to a particular alert mode. The instructions may cause processing circuitry 210 to select a particular alert mode based on the type of condition. For example, the instructions may associate a seizure with a first alert mode and a battery level indicator with a second, and different, alert mode. The instructions may include escalation alert modes, which may combine alert modes or increase intensity of an alert mode. After selecting the alert mode, processing circuitry 210 may cause other circuitry to output, in the selected alert mode, an alert, e.g., a notification that indicates the condition occurred, or responds to patient input, output an indication of charging status, battery level, and so on.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 26. In other examples, stimulation generation circuitry 202 and/or sensing circuitry 26 may include sensing circuitry to direct signals to and/or from one or more of electrodes 232, 234, which may or may not also include switch circuitry 204.

As described above in relation to FIG. 1, in some examples, stimulation generation circuitry 202 may be configured to deliver electrical stimulation therapy as well as notification stimulation. In some examples, processing circuitry 210 may cause stimulation generation circuitry 202 to interleave the notification stimulation with the stimulation therapy. In some examples, stimulation generation circuitry may deliver the notification stimulation as housing stimulation above a perception level of the patient at the implant site of IMD 200. In other examples, an electrode on a lead, such as electrode 242 on lead 243, may implanted proximal to the implant site, and the electrode may act as a cathode to deliver the notification stimulation. For example, stimulation generation circuitry 202 may deliver electrical stimulation therapy pulses to the patient via one or more the electrodes on leads 230. Stimulation generation circuitry 202 may interleave notification stimulation using some other combination of electrodes, e.g., including the housing.

In other examples, an electrode integrated with the housing of the implantable medical device but electrically isolated from the housing may act as a cathode to deliver the notification stimulation. For example, switch circuitry 204 may connect electrode 246 to stimulation generation circuitry 202 as part of the second electrode combination described above in relation to FIG. 1, to deliver the notification stimulation. In this disclosure, the housing of IMD 200, (e.g., depicted in as 110 in FIG. 1, but not shown in FIG. 2) may contain and protect from the elements the electronics and other components of IMD 200 shown in FIG. 2. In some examples, electrode 246 may be also be a portion of the housing, or attached to the housing or the header, as described above in relation to FIG. 1. In some examples switch circuitry 204 may connect electrode 242, the housing and/or electrode 246, in some combination to stimulation generation circuitry 202, to deliver the notification stimulation, based on commands from processing circuitry 210.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. Additionally, or alternatively, sensing circuitry 206 may sense one or more stimulation pulses delivered to patient 105 via electrodes 232, 234. In some examples, sensing circuitry 206 detects bioelectrical signals from a particular combination of electrodes 232, 234. Sensing circuitry 206 may provide signals to an analog-to-digital converter, for conversion into a digital signal for processing, analysis, storage, or output by processing circuitry 210.

Communication circuitry 208, in the example of FIG. 2, supports communication, including wireless communication, between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the therapy stimulation programs 214 and alert instructions 216 may be stored within storage device 212. Communication circuitry 208 in IMD 200, as well as communication circuits in other devices and systems described herein such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1. Accordingly, communication circuitry 208 may send information to the external programmer on a continuous basis, at periodic intervals, or upon request from IMD 200 or the external programmer. In some examples, communication circuitry 208 may also support communication between other medical devices, e.g., IMD 125 described above in relation to FIG. 1, either implanted in, worn by or in proximity to patient 105 depicted in FIG. 1.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software, or any combination thereof. Processing circuitry 210 controls stimulation generation circuitry 202 to generate stimulation signals according to therapy stimulation programs 214 and alert instructions 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 may also control stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

In some examples, one or more of electrodes 232 and 234 are suitable for sensing stimulation signals. For instance, electrodes 232 and 234 may sense the voltage amplitude of a portion of the stimulation signals, where the sensed voltage amplitude is a characteristic of the stimulation signals. In some examples, one or more of electrodes 232 and 234 may sense a stimulation signal in response to one or more of electrodes 232 and 234 delivering a stimulation pulse to target tissue of patient 105. In some examples, the one or more of electrodes 232 and 234 which sense the stimulation signal are not the same as the one or more of electrodes 232 and 234 which deliver the stimulation pulse.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214, alert instructions 216.

Determining therapy based on one or more stimulation signals may, in some cases, depend on a posture of patient 105. For example, processing circuitry 210 may be configured to determine a posture of patient 105 based on an acceleration signal generated by acceleration sensor 223. In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. It may be beneficial for processing circuitry 210 to analyze one or more of the vertical axes, the lateral axis, and the frontal axis in order to determine a posture of patient 105.

In some examples, acceleration sensor 223 is a movement sensor configured to generate an accelerometer signal. Processing circuitry 210 is configured to identify, based on the accelerometer signal, a posture of a set of postures which patient 105 is occupying. The set of postures may include, for example, a standing posture, a sitting posture, a supine posture, a prone posture, a side-lying posture, or any combination thereof. In some examples, expected parameter values of the accelerometer signal corresponding to each posture of the set of postures are stored in storage device 212. Subsequently, processing circuitry 210 may select, based on the identified posture, a target stimulation signal value (e.g., a target range of characteristic values) for a stimulation signal sensed by IMD 200 in response to a delivery of a corresponding stimulation pulses. For example, if stimulation generation circuitry 202 generates a stimulation pulse having a stimulation amplitude and delivers the stimulation pulse to target tissue of patient 105 via one or a combination of electrodes 232, 234, processing circuitry 210 may select, based on a posture of patient 105 during the delivery of the stimulation pulse, a target range for a characteristic of the resulting stimulation signal sensed by sensing circuitry 206. Subsequently, processing circuitry 210 may determine whether to change one or more parameters of therapy stimulation programs 314 and/or alert instructions 216 based on whether the characteristic value is within the target range of characteristic values selected based on the posture of patient 105.

As described above in relation to FIG. 1, acceleration sensor 223 may be configured to detect movement that may represent a communication, e.g., from patient 105. In some examples, the communication may include one or more taps on a housing of IMD 200. The acceleration sensor 223 may detect the one or more taps as one or more movements in a single direction exceeding a threshold, where movement may include velocity, acceleration, change in accelerations and so on. In other examples, acceleration sensor 223 may detect more jiggle movements of the housing of IMD 110, or a separate movement sensor. The movement sensor may be configured to detect the one or more jiggle movements as one or more movements in opposite directions exceeding a threshold. Based on the signals from acceleration sensor 223, processing circuitry 210 may determine that the detected movements are a communication, further determine the nature of communication based on the pattern of movements, and select the action to perform, based on the determined communication. In some examples the action may include to simply responds to acknowledge the received communication by selecting one or more of the alert modes described above. In other examples, the actions may include one or more additional actions. For example, processing circuitry 210 may receive a communication to change a sensing mode. Based on the decoded tapping or jiggle message, processing circuitry 210 may change the sensing mode and to output an alert indicating that the sensing mode has changed. In another example, processing circuitry 210 may receive a communication to change a therapy mode or some other aspect of delivered therapy. Based on the received communication, processing circuitry may output a notification, using a preselected alert mode, to indicate that the therapy has changed.

In some examples, IMD 200 may also include vibration and audio generator 209. Processing circuitry 210 may cause vibration and audio generator 209 to output tones, vibration, or some combination of both in a variety of patterns and frequencies. In some example the selection of alert mode may depend on the patient's tactile sensitivity and auditory acuity. In other examples, vibration and audio generator 209 may include only one of a vibration generator or an audio generator.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
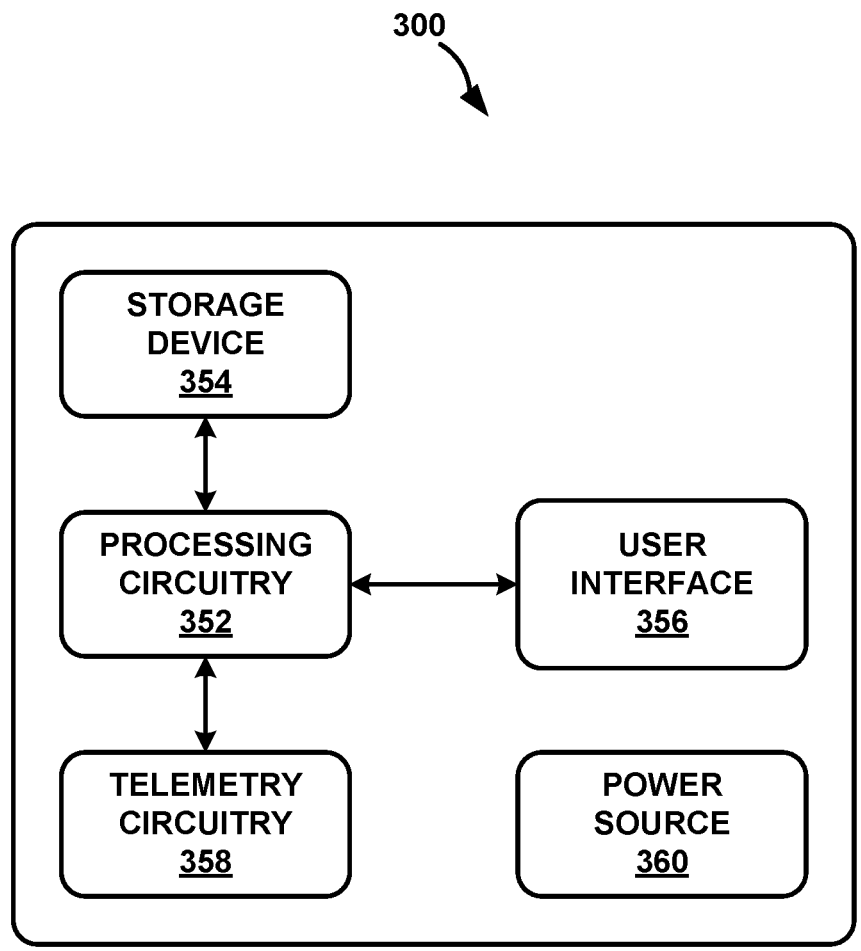
FIG. 3 is a block diagram illustrating an external device configured to communicate with a medical device and receive and deliver notifications according to one or more techniques of this disclosure.

FIG. 3 is a block diagram illustrating an external device configured to communicate with a medical device and receive and deliver notifications according to one or more techniques of this disclosure. FIG. 3 depicts an example configuration of components of external device 300 may be an example of external device 150 of FIG. 1. Although external device 300 may generally be described as a hand-held device, external device 300 may be a larger portable device or a stationary device. In addition, in other examples, external device 300 may be included as part of an external charging device or include the functionality of an external charging device. In some examples, external device 300 may include a software application running on a multi-purpose device, e.g., a smart phone, laptop computer, tablet computer and so on.

As illustrated in FIG. 3, external device 300 may include processing circuitry 352, storage device 354, user interface 356, telemetry circuitry 358, and power source 360. Storage device 354 may store instructions that, when executed by processing circuitry 352, cause processing circuitry 352 and external device 300 to provide the functionality ascribed to external device 300 throughout this disclosure. Each of these components, circuitry, or modules, may include electrical circuitry that is configured to perform some, or all of the functionality described herein. For example, processing circuitry 352 may include a processor configured to perform the processes discussed with respect to processing circuitry 352.

In general, external device 300 includes any arrangement of hardware, alone or in combination with software and/or firmware, configured to perform the techniques attributed to external device 300, and processing circuitry 352, user interface 356, and telemetry circuitry 358 of external device 300. In various examples, external device 300 may include one or more processors, such as one or more microprocessors, DSPs, ASICs, FPGAs, or any other equivalent integrated or discrete logic circuitry, as well as any combinations of such components. External device 300 also, in various examples, may include a storage device 354, such as RAM, ROM, PROM, EPROM, EEPROM, flash memory, a hard disk, a CD-ROM, which may store executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device or memory) may store instructions that, when executed by processing circuitry 352, cause processing circuitry 352 and external device 300 to provide the functionality ascribed to external device 300 throughout this disclosure. For example, storage device 354 may include instructions that cause processing circuitry 352 to obtain a parameter set from memory or receive a user input and send a corresponding command to IMD 110 described above in relation to FIG. 1, or instructions for any other functionality. In addition, storage device 354 may include a plurality of programs, where each program includes a parameter set that defines stimulation pulses, notification stimulation, communication details and so on. Storage device 354 may also store data received from a medical device (e.g., IMD 110). For example, storage device 354 may store the instructions for the various selectable alert modes described above in relation to FIG. 1, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a presence-sensitive screen (e.g., a touch screen). User interface 356 may be configured to display any information related to the delivery of electrical stimulation, identified patient behaviors, sensed patient parameter values, patient behavior criteria, or any other such information. User interface 356 may also receive user input via user interface 356. The input may be, for example, in the form of pressing a button on a keypad or selecting an icon from a touch screen.

In some examples, the input from the user may request starting or stopping electrical stimulation, or some other change to the delivery of electrical stimulation. For example, the input may request an increase or decrease to stimulation intensity (e.g., amplitude, pulse width, or frequency). Device 300 can then transmit these requests to IMD 20. Device 300 may receive, and transmit, the input requesting changes to one or more parameter values that configure IMD 110 or IMD 125 depicted in FIG. 1. For example, responsive to the input, processing circuitry 352 may configure the instructions in the memory, e.g., storage unit 354 or storage device 212 described above in relation to FIG. 2, based on the information that processing circuitry 352 received from user interface 356.

In some examples, processing circuitry 352 may control user interface 356 to display a guided setup, e.g., a software wizard, to aid a user in configuring IMD 110 or IMD 125. For example, user interface 356 may receive a user input indicating the patient ability to detect one or more of the alert modes. Processing circuitry 352 may compare the received input to instructions stored at storage device 354 and cause a display of user interface 356 to provide a recommended alert mode based on the patient ability. For example, user interface 356 may receive an input describing a patient's hearing acuity, tactile sensitivity, visual acuity, and so on. Based on the received patient's abilities, processing circuitry 352 may cause user interface 356 to display one or more recommended alert modes. The user, e.g., a clinician, caregiver, or the patient, may select or decline the recommended alert modes. In other examples, user interface 252 may receive a user input describing other devices implanted in or worn by the patient, e.g., a cochlear implant, hearing aid, fitness tracker and so on. Based on the received input, processing circuitry 352 may recommend alert modes that take advantage of the other devices. For example, for a patient that regularly wears a fitness tracker with a text display capability, processing circuitry 352 may recommend a text display, or vibration alert be sent to the fitness tracker. Processing circuitry may further request information, to cause the medical device to communicate with the fitness tracker, e.g., a wireless address and pass code. Other examples of external devices may include text messaging, communicate with a smart speaker, and so on.

In other examples, user interface 356 may be configured to receive an input to cause the implantable medical device to set a first selected alert mode of the plurality of alert modes as the default alert mode. In other words, external device 300 may communicate with a medical device, e.g., via telemetry circuitry 358 and, based on a user selection, send commands to program the medical device to set an alert mode as the default alert mode. In some examples, user interface 356 may be configured to receive an input to cause the implantable medical device to assign a first selected alert mode of the plurality of alert modes to a first detected condition and to assign a second selected alert mode of the plurality of alert modes to a second detected condition. For example, based on instructions from external device 300, an implantable medical device (e.g., IMD 110) may assign a first alert mode, a signal to the patient's auditory nerve along a body network pathway, to bladder filling notification, and a second alert mode, e.g., a notification stimulation at the implant site, to a change in electrical stimulation therapy mode. Similarly, processing circuitry 352 may cause different alert modes to be assigned to different conditions of the implantable medical device, such as detected noise, battery level, or a detected device malfunction including one or more of: lead break, memory error, a communication issue and so on. Also, as described above in relation to FIG. 1, based on inputs from user interface 356, processing circuitry 352 may assign different alert modes cause the implantable medical device to output the alert based on a physiological event with the patient. Examples of physiological events may include one or more of: a gait freeze; a local field potential (LFP) threshold exceeded, a seizure; a bladder fullness, and a missed medication dose and other patient conditions. User interface 356 may also receive an input to configure the implantable medical device to output the alert based on an action taken by the implantable medical device, e.g., changing sensing mode, therapy, as well as sending a message to the patient's medical provider and a confirmation of a patient input, e.g., a pattern of taps on the housing. Some examples of alerts may include an epilepsy seizure alert, elevation in inter-ictal spiking alert, SUDEP alert, take medication alert or a fall alert.

In other examples, an input to user interface 356 may set an alert mode as an escalation alert mode. As described above in relation to FIG. 1, an escalation alert mode may be a second, third or later notification in a series of notifications, such as battery charging needed. A first notification may use a selected alert mode to indicate the battery level is at, for example, 20%, while an escalation alert mode may indicate a battery level at 15%. For example, for a tremor patient, it could be that the therapy is turned off for 10 seconds when the battery is at 20%, but at the 10% level it turns off differently (for a longer period or 2 times for 10 seconds). An escalation alert mode may include higher magnitude, more repetitions, faster pulse repetition rate and so on than the originally selected alert mode. In other examples, an escalation alert mode may include a different patient alert modality, e.g., switch from an audible tone alert mode to a vibration alert mode. In other examples, the escalation alert mode may include two or more alert modalities at same time and/or interleaving two or more patient alert modalities.

User interface 356 may be configured to receive an input to cause the implantable medical device to withhold an alert, e.g., a notification using a particular alert mode, based on an activity level of the patient. In some examples, the activity level may include a consciousness level of the patient, e.g., while the patient is sleeping, in a coma, under anesthesia, and so on. In other examples, inputs to user interface 356 may cause the implantable medical device to withhold the alert based on a time of day, such as when the patient is sleeping.

In some examples, user interface 356 may be configured to receive an input to cause the implantable medical device to output a selected alert mode. For example, after receiving a device, a clinician may help the patient select and recognize various notifications based on selected alert modes. An input to user interface 356 may cause an implantable, or wearable, medical device, to output a notification in a selected alert mode, e.g., a pattern of notification stimulation pulses at the implant site. During such a training session, the patient and clinician may output various alert modes to make sure the patient recognizes and can respond to the notification. In some examples, user interface 356 may present a confirmation button that requires the patient or user to select the confirmation button after the notification has been detected by the patient. User interface 356 may increase or otherwise vary the intensity of an alert mode until the confirmation button is selected and set the intensity at the latest intensity level that elicited selection of the confirmation button. Similarly, in some examples, user interface 356 may be configured to receive an input to cause the implantable medical device to repeat a most recently output alert. For example, the patient may want to confirm that an apparent sound, vibration, change in therapy, and so on, was a notification, rather than something else. By repeating the most recent notification, the patient may determine whether the sensation, sound, etc. was a notification in a particular alert mode.

Telemetry circuitry 358 may support wireless communication between the medical device and external device 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external device 300 and IMD 11 include RF communication according to the 802.11 or Bluetooth® specification sets, Wi-Fi or other standard or proprietary telemetry protocols. In this manner, other external devices may be capable of communicating with external device 300 without needing to establish a secure wireless connection. As described herein, telemetry circuitry 358 may be configured to transmit a spatial electrode movement pattern or other stimulation parameter values to IMD 11 for delivery of electrical stimulation therapy.

Power source 360 is configured to deliver operating power to the components of external device 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external device 300. In other examples, traditional batteries (e.g., nickel cadmium or lithium ion batteries) may be used. In addition, external device 300 may be directly coupled to an alternating current outlet to operate.

Figure 4:
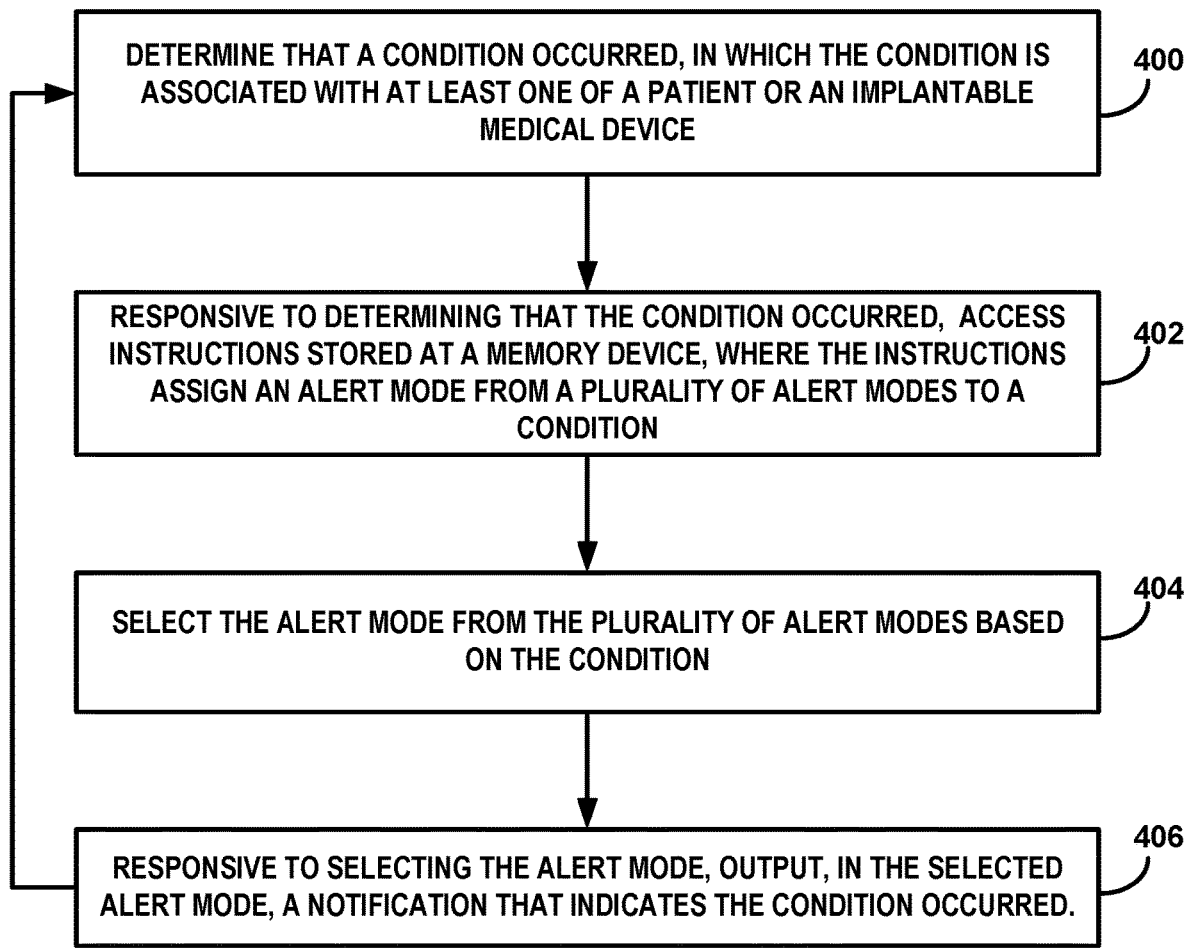
FIG. 4 is a flowchart illustrating an example operation of the medical system of this disclosure to select an alert mode and output a notification according to the selected alert mode.

FIG. 4 is a flowchart illustrating an example operation of the medical system of this disclosure to select an alert mode and output a notification according to the selected alert mode. The blocks of FIG. 4 will be described as being performed by components of IMD 200 of FIG. 2, such as processing circuitry 210, unless otherwise noted. In other examples, other devices, components, or combinations of devices and/or components may perform the operation of FIG. 4.

In the example of FIG. 4, processing circuitry 210 of IMD 200 may determine that a condition occurred (400). The condition may be associated with at least one of a patient or of implantable medical device 200. As described above in relation to FIGS. 1-3, patient conditions may include consciousness level, epileptic activity, and so on. Device conditions may include memory or communication error, battery recharge level and similar device conditions. Processing circuitry 210 may determine that the condition occurred by monitoring one or more sensors for the patient and/or operations of IMD 200.

Responsive to determining that the condition occurred, processing circuitry 210 may access instructions for selecting an alert mode from a plurality of alert modes (402). The instructions may be stored at the memory, e.g., storage device 212. Based on the instructions stored at storage device 212, e.g., instructions that assign a particular condition to a particular alert mode, processing circuitry 210 selects the alert mode from the plurality of alert modes based on the detected condition (404).

Responsive to selecting the alert mode, processing circuitry 210 may cause one or more components of IMD 200 to output the notification in the selected alert mode to alert the patient, a caregiver, etc. that the condition occurred (406). For example, stimulation generation circuitry 202 may output a notification stimulation at the implant site or may change the delivered therapy such that the patient detects the change. Communication circuitry 208 may send the notification to an external device. In some examples, processing circuitry may output the alert via a body network pathway. Processing circuitry 210 may continue to monitor for the condition after causing the notification to be sent. In some examples, processing circuitry may repeat the notification, escalate the notification, and so on depending on the determined condition, if processing circuitry 210 again senses the condition.

Figure 5:
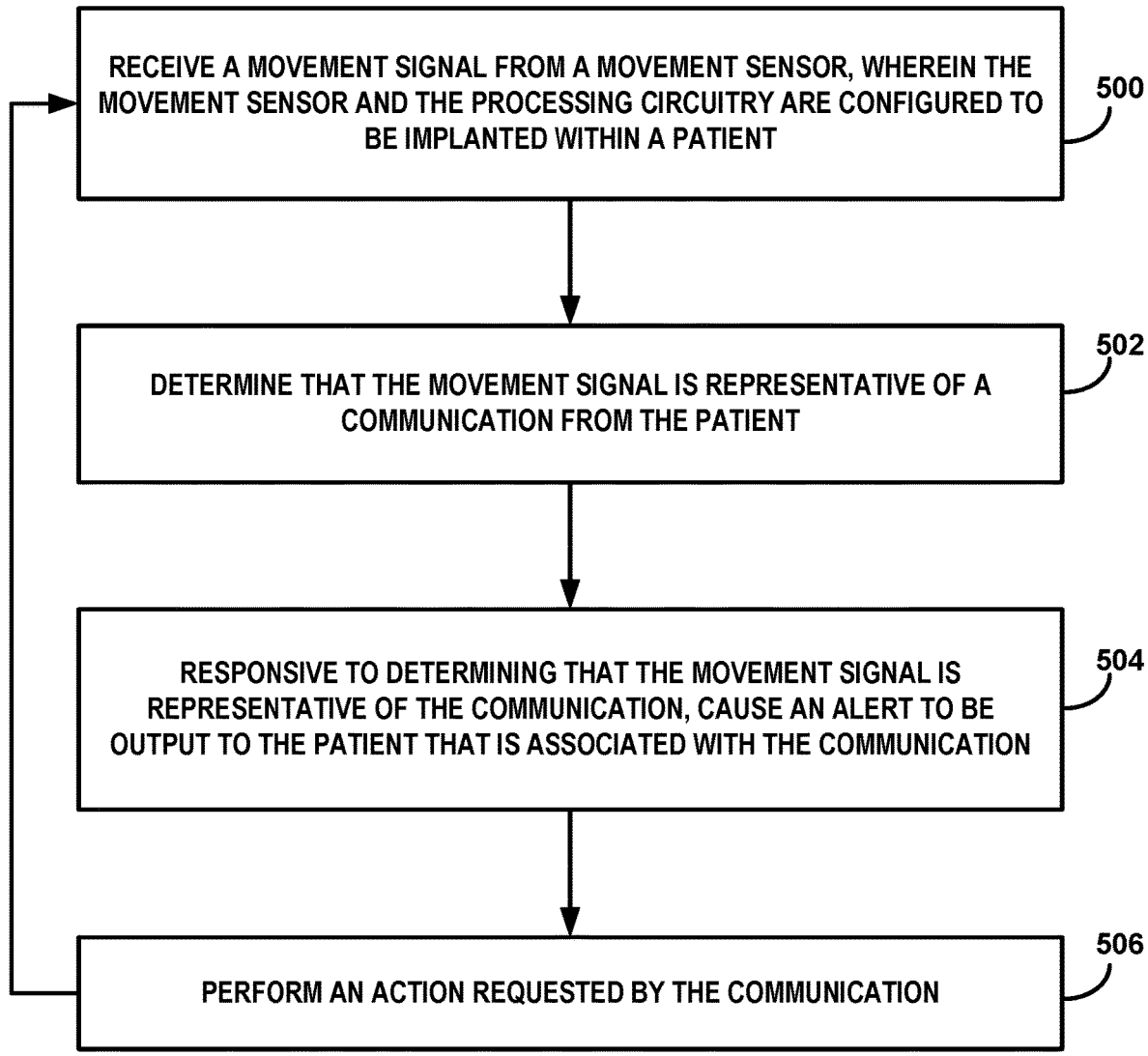
FIG. 5 is a flow chart illustrating an example operation of the medical system of this disclosure to receive a communication in the form of a movement signal and output a notification in response to the received communication.

FIG. 5 is a flow chart illustrating an example operation of the medical system of this disclosure to receive a communication in the form of a movement signal and output a notification in response to the received communication. The blocks of FIG. 5 will be described as being performed by components of IMD 200 of FIG. 2, such as processing circuitry 210, unless otherwise noted. In other examples, other devices, components, or combinations of devices and/or components may perform the operation of FIG. 5.

In the example of FIG. 5, processing circuitry 210, which is part of IMD 200 configured to be implanted within a patient, may receive a movement signal from a movement sensor, e.g., movement sensor 222 (500). The movement sensor may also be configured to be implanted within the patient. In some examples, the processing circuitry and movement sensor may be within a housing of an implantable medical device, e.g., IMD 110 described above in relation to FIG. 1 and IMD 200 depicted in FIG. 2. In other examples, the movement sensor may be separate from the implantable medical device and also implanted within the patient. The processing circuitry may also be separate from the implantable medical device. For example, a movement sensor, e.g., an accelerometer, may be available to the patient and may communicate with processing circuitry in an external device, e.g., external device 150 described above in relation to FIG. 1.

In the example of FIG. 5, processing circuitry 210 receives a movement signal from acceleration sensor 223 and determine that the movement signal is representative of a communication from the patient (502). As described above in relation to FIGS. 1 and 2, processing circuitry 210 may determine that the movement signal may be representative of a pattern of taps or jiggles of the housing of IMD 200 that corresponds to communication from the patient. The communication may include requests for information, e.g., a battery discharge level, therapy, or sensing mode, etc. In other examples, the communication may be a command to change therapy mode, turn therapy on or off, turn sensing on or off, identify that an event occurred, and so on.

Responsive to determining that the movement signal is representative of the communication, processing circuitry 210 may cause an alert to be output to the patient that is associated with the communication (504). Processing circuitry 210 then also performs the action requested by the communication (506). In some examples, the alert may confirm, by processing circuitry 210, that the communication was received or indicate the requested action was performed. Processing circuitry 210 may continue to monitor for the condition after causing the alert to be sent (504) and performing the action (506), if applicable.

In some examples, processing circuitry 210 may cause an acknowledgement notification (504) to be output in one alert mode while the indication that the action was performed is output in a different alert mode. Processing circuitry 210 may first perform the request action and then cause the alert to the delivered to the patient only after the action is completed. In this manner, the alert may be delayed for seconds, minutes, or even hours in some cases. In other examples, processing circuitry 210 may perform the requested action without also causing an alert to the output to the patient. In one example, the action may be detectable by the patient, such as a change in therapy or turning therapy on or off, and an alert representative or the requested action may not be necessary. Processing circuitry 210 may selectively cause the alert to be delivered (e.g., whether or not the alert is delivered, or the type of alert mode used for the alert) based on the type of action that has been requested.

Figure 6:
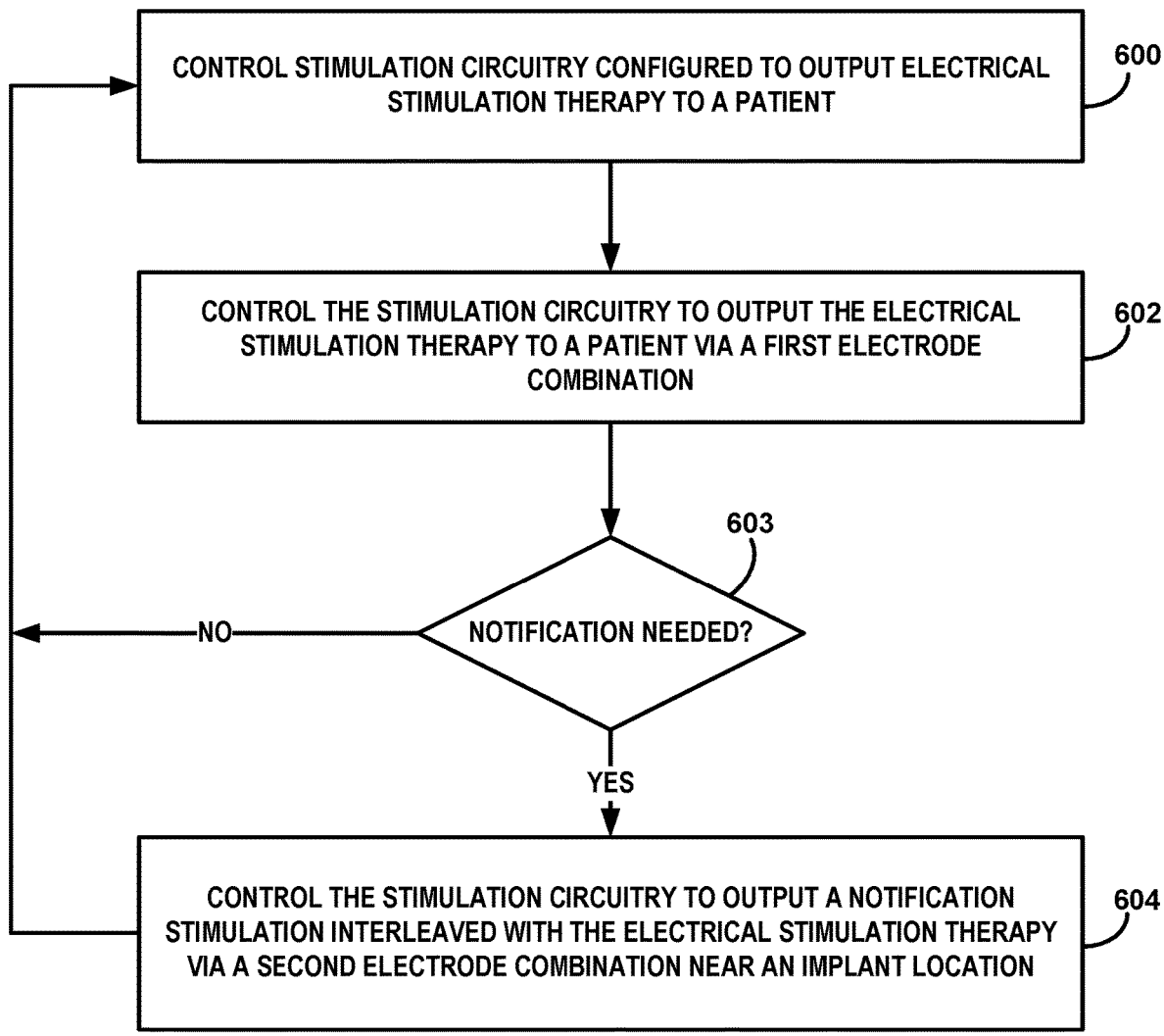
FIG. 6 is a flow chart illustrating an example operation of the medical system of this disclosure to output a notification stimulation above a perception level of the patient that is interleaved with the electrical stimulation therapy.

FIG. 6 is a flow chart illustrating an example operation of the medical system of this disclosure to output a notification stimulation above a perception level of the patient that is interleaved with the electrical stimulation therapy. The blocks of FIG. 6 will be described as being performed by components of IMD 200 of FIG. 2, such as processing circuitry 210, unless otherwise noted. In other examples, other devices, components, or combinations of devices and/or components may perform the operation of FIG. 6.

In the example of FIG. 6. processing circuitry 210 may control stimulation generation circuitry 202 to generate and delivery (e.g., output) electrical stimulation therapy to a patient (600). Switch circuitry 204 may output the electrical stimulation therapy to the patient, e.g., patient 105 depicted in FIG. 1, via a first electrode combination (602). The first electrode combination may include any one or more of electrodes 232, 234, a housing electrode (not shown in FIG. 2), an integrated electrode 246, e.g., an indifferent electrode, an electrode on a lead extension 243, or some other combination. The electrical stimulation therapy may provide pain relief, or other therapy to address a medical condition of patient 105.

Processing circuitry 210 may determine whether processing circuitry 210 should output a notification, e.g., based on detecting a condition, receiving an input from a user that should be acknowledged, and so on (603). When no notification is needed (NO branch of 603) processing circuitry may continue to deliver therapy stimulation as programmed.

When notification is needed (YES branch of 603), processing circuitry 210 also controls stimulation generation circuitry 202 to output a notification stimulation interleaved with the electrical stimulation therapy via a second electrode combination (604). As described above in relation to FIGS. 1-2, the notification stimulation may define an intensity above a perception level of patient 105. In some examples, the second electrode combination comprises an electrode disposed at an implant site e.g., in or near tissue pocket 112 described above in relation to FIG. 1, of the implantable medical device. The electrode at the implant site may act as a cathode for the notification stimulation and may include any one or more of: a conductive portion of the housing, a separate electrode 246 on the housing, or electrode 242 on lead 243 implanted proximal to tissue pocket 112.

In some examples, to interleave an alert, processing circuitry 210 may cause a notification stimulation to be inserted in a timing duration between therapy stimulation pulses. In some examples a notification stimulation may use the same output electrodes as the therapy stimulation pulses, and may be output, for example, as a higher magnitude therapy pulse instead of the programmed therapy pulse. In other examples, the notification stimulation may be delivered from a different set of electrodes than the therapy stimulation, e.g., a notification stimulation via the housing at the implant site, in a time duration between therapy stimulation. In other examples, processing circuitry 210 may briefly pause therapy stimulation, e.g., for a few milliseconds, so that stimulation generation circuitry 202 may instead output a notification stimulation above the perception threshold of the patient during the pause. In other examples, an interleaved alert may include a stimulation change that results in side effects. Side effects could involve over-stimulation side effects or under-stimulation side effects.

Figure 7:
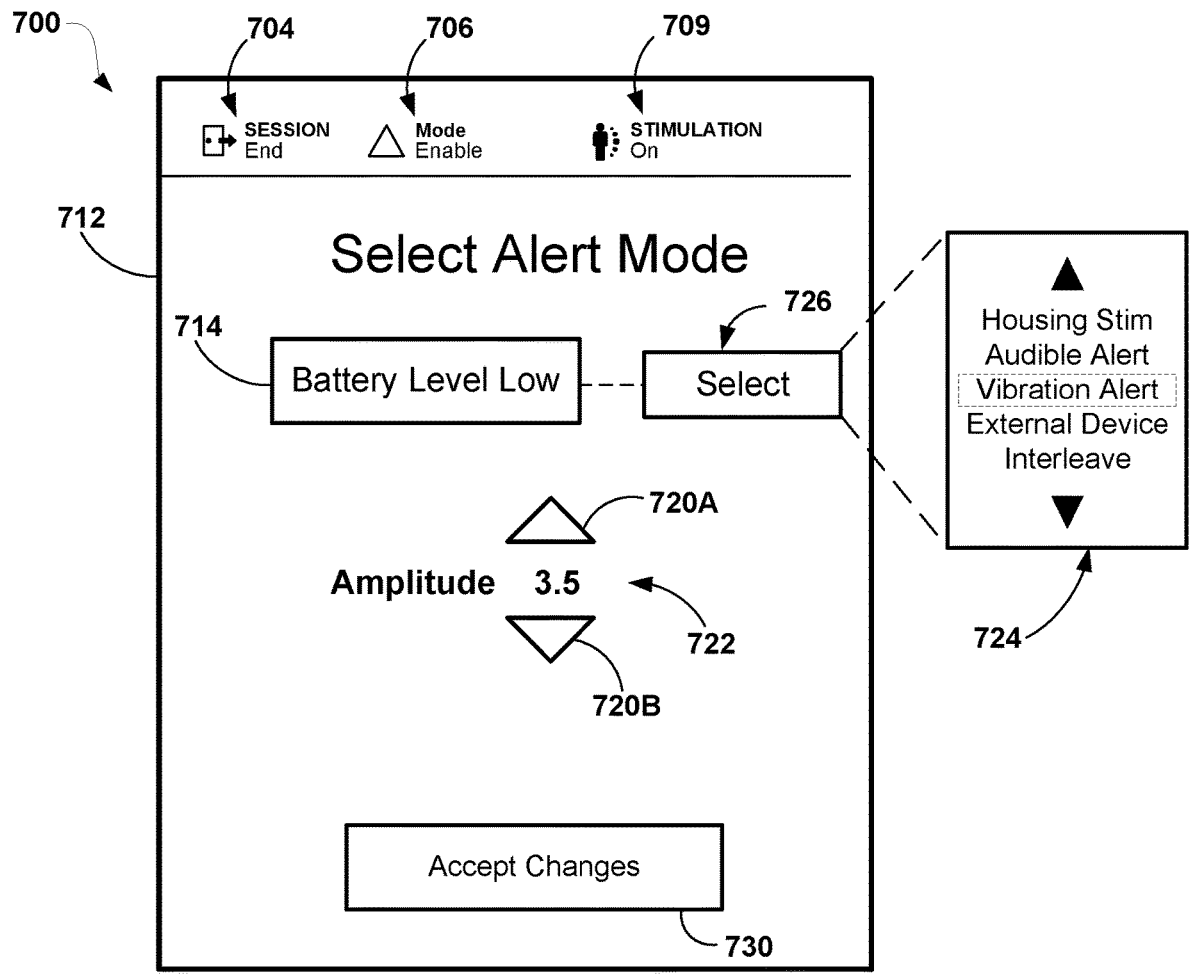
FIG. 7 is a conceptual diagram illustrating an example user interface for configuring alert modes for a device.

FIG. 7 is a conceptual diagram illustrating an example user interface for configuring alert modes for a device. User interface 700 may be an example of user interface 356 described above in relation to FIG. 3 and include similar functions and characteristics. Although user interface 700 may typically be used for a patient programmer and used by a patient, user interface 700, alternatively or additionally, may be presented in a clinician programmer or remote device in other examples. Moreover, user interface 700 is generally described as being presented via a touchscreen device. However, one or more features of user interface 700 may be implemented with one or more inputs having switches, dials, slides, buttons, keypads, or any other mechanisms separate from a touchscreen display.

As shown in the example of FIG. 7, processing circuitry 352 of external device 300 my cause a display 712 to provide example user interface 700 to the user, such as a clinician. User interface 700 may include features to, for example, assign a selected alert mode of the plurality of alert modes to a detected condition. Screen 712 includes session end button 704, Mode toggle 706, and stimulation therapy toggle 709. Screen 712 also includes condition selection button 714, alert mode selection button 726, amplitude value indicator 722, amplitude adjustments 720A and 720B and accept changes button 730.

In operation, a user may use condition selection 714 to scroll through a variety of conditions, as described above in relation to FIGS. 1-6. The example of FIG. 7 displays a "battery level low" condition. Once the user selects the condition, alert mode selection button 726 may present a scrollable display 724 with different options for alert modes. Once the user selects an alert mode for the displayed condition, the user may customize the alert mode, such as by changing an amplitude adjustments 720A and 720B. In some examples, processing circuitry 352 may cause user interface 700 to display different adjustment options depending on the selected alert mode. For example, in addition to an amplitude adjustment, an audible alert may also include selection options for frequency, tone, pattern and so on. A selection of "external device" in selection button 726 may cause display 712 to present input selectors for type of external device, name of external device, output options for the external device, and so on (not shown in FIG. 7). In some examples, screen 712 or another screen of user interface 700 may provide a selectable button that, when selected, causes the system to request that the medical device generates an example notification to what was selected by the user. In this manner, the user can sample, or try out, different alert modes and/or amplitudes of each alert mode. In some examples, user interface 700 may provide a training mode in which the system can help train the user to identify the one or more different alert modes that were predetermined or selected by the user.

In one or more examples, the functions described above may be implemented in hardware, software, firmware, or any combination thereof. For example, the various components of FIGS. 2 and 3, such as IMD 200, processing circuitry 210, communication circuitry 208, processing circuitry 352 and so on may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache).

By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, such as processing circuitry 210, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The techniques of this disclosure may also be described in the following examples.

Example 1: A medical system includes a memory configured to store instructions for selecting an alert mode from a plurality of alert modes; and processing circuitry configured to: determine that a condition occurred, the condition associated with at least one of a patient or an implantable medical device; responsive to determining that the condition occurred, select the alert mode from the plurality of alert modes based on the condition, and the instructions; and responsive to selecting the alert mode, output, in the selected alert, an alert that indicates the condition occurred.

Example 2: The medical system of example 1, further comprising a user interface configured to: receive an input; responsive to the input, configure the instructions in the memory.

Example 3: The medical system of examples 1 and 2, wherein to select an alert mode further depends on the patient's ability to detect one or more alert modes of the plurality of alert modes.

Example 4: The medical system of any combination of examples 1-3, wherein the patient ability comprises a hearing acuity of the patient and a tactile sensitivity of the patient.

Example 5: The medical system of any combination of examples 1-4, comprising an implantable medical device, wherein the implantable medical device comprises the processing circuitry and the memory.

Example 6: The medical system of any combination of examples 1-5, wherein the plurality of alert modes comprises one or more of: a vibration of the implantable medical device; an audio sound generated by the implantable medical device; and a communication to a device external to the implantable medical device.

Example 7: The medical system of any combination of examples 1-6, wherein the plurality of alert modes comprises housing stimulation, wherein the processing circuitry is configured to cause a sensation above a perception threshold of the patient between a housing of the implantable medical device and tissue of the patient at an implant site of the implantable medical device.

Example 8: The medical system of any combination of examples 1-7, wherein the plurality of alert modes comprises a modification to stimulation therapy delivered by the implantable medical device, wherein the modification to the stimulation therapy comprises one or more of: withhold the stimulation therapy for a predetermined duration; change intensity of the stimulation therapy for the predetermined duration; interleave an alert signal with the stimulation therapy for the predetermined duration.

Example 9: The medical system of any combination of examples 1-8, wherein the medical system is configured to modify the stimulation therapy in a predetermined pattern.

Example 10: The medical system of any combination of examples 1-9, wherein the plurality of alert modes comprises sending a signal through a body network pathway of the patient.

Example 11: The medical system of any combination of examples 1-10, wherein the patient's auditory nerve receives the signal through the body network pathway and wherein the received signal causes the auditory nerve to provide an apparent audible alert to the patient.

Example 12: The medical system of any combination of examples 1-11, wherein the implantable medical device is a first implantable medical device, wherein the medical system comprises second medical device in the same patient, wherein the second medical device receives the signal through the body network pathway, and wherein the second medical device provides the alert to the patient.

Example 13: The medical system of any combination of examples 1-12, wherein the condition detected by the processing circuitry comprises a condition of the implantable medical device, and wherein the condition of the implantable medical device comprises one or more of: low battery, or recharge status.

Example 14: The medical system of any combination of examples 1-13, wherein the condition detected by the processing circuitry comprises a condition of the implantable medical device, and wherein the condition of the implantable medical device is a device malfunction comprising one or more of: lead break detected, memory error, and a detected communication issue.

Example 15: The medical system of any combination of examples 1-14, wherein the condition detected by the processing circuitry comprises a consciousness condition of the patient, and wherein the processing circuitry is configured to detect the consciousness condition and to withhold the alert when the processing circuitry detects that the consciousness condition of the patient comprises one or more of: sleeping, and a coma.

Example 16: The medical system of any combination of examples 1-15, wherein the condition detected by the processing circuitry comprises an activity level of the patient, and wherein the processing circuitry is configured to withhold the alert based on the patient's activity level.

Example 17: The medical system of any combination of examples 1-16, wherein the condition detected by the processing circuitry comprises a physiological event with the patient, and wherein the detected physiological event comprises one or more of: a gait freeze; a local field potential (LFP) threshold exceeded, a seizure; a bladder fullness, and a missed medication dose.

Example 18: The medical system of any combination of examples 1-17, wherein the condition detected by the processing circuitry is based on an action taken by the processing circuitry, and wherein the action taken by the processing circuitry comprises one or more of: a confirmation of a patient input and sending a message to the patient's medical provider.

Example 19: A method includes determining, by processing circuitry operatively coupled to a memory, that a condition occurred, the condition associated with at least one of a patient or an implantable medical device; responsive to determining that the condition occurred, accessing, by the processing circuitry, instructions stored at the memory for selecting an alert mode from a plurality of alert modes, and selecting the alert mode from the plurality of alert modes based on the condition; responsive to selecting the alert mode, outputting, in the selected alert mode, an alert that indicates the condition occurred.

Example 20: The method of example 19, wherein the processing circuity is operatively coupled to a user interface, the method further includes receiving, by the user interface, an input to configure the instructions stored at the memory, receiving, by the processing circuitry, information from the user interface to configure the instructions, and configuring the instructions stored at the memory.

Example 21: The method of any combination of examples 19-20, wherein selecting the alert is further based on the patient's ability to detect one or more alert modes of the plurality of alert modes.

Example 22: The method of any combination of examples 19-21, further includes receiving, by the user interface, an input regarding the patient ability, and providing a recommended alert mode based on the patient ability.

Example 23: The method of any combination of examples 19-22, wherein the patient ability comprises a hearing acuity of the patient and a tactile sensitivity of the patient.

Example 24: The method of any combination of examples 19-23, wherein the user interface is configured to receive an input to cause the implantable medical device to set a first selected alert mode of the plurality of alert modes as the default alert mode.

Example 25: The method of any combination of examples 19-24, wherein the user interface is configured to receive an input to cause the implantable medical device to set a second selected alert mode of the plurality of alert modes as an escalation alert mode.

Example 26: The method of any combination of examples 19-25, wherein the user interface is configured to receive an input to cause the implantable medical device to assign a first selected alert mode of the plurality of alert modes to a first detected condition and to assign a second selected alert mode of the plurality of alert modes to a second detected condition.

Example 27: The method of any combination of examples 19-26, wherein the user interface is configured to receive an input to cause the implantable medical device to withhold the alert based on an activity level of the patient.

Example 28: The method of any combination of examples 19-27, wherein the activity level comprises a consciousness level of the patient.

Example 29: The method of any combination of examples 19-28, wherein the user interface is configured to receive an input to cause the implantable medical device to withhold the alert based on a time of day.

Example 30: The method of any combination of examples 19-29, wherein the user interface is configured to receive an input to cause the implantable medical device to output the selected alert mode.

Example 31: The method of any combination of examples 19-30, wherein the user interface is configured to receive an input to cause the implantable medical device to repeat a most recently output alert.

Example 32: The method of any combination of examples 19-31, wherein the user interface is configured to receive an input to cause the implantable medical device to output the alert based a consciousness condition of the patient, and wherein the implantable medical device is configured to withhold the alert when the implantable medical device detects that the consciousness condition of the patient comprises one or more of: sleeping, and a coma.

Example 33: The method of any combination of examples 19-32, wherein the user interface is configured to receive an input to cause the implantable medical device to output the alert based a condition of the implantable medical device, and wherein the condition of the implantable medical device comprises one or more of: low battery, or recharge status.

Example 34: The method of any combination of examples 19-33, wherein the user interface is configured to receive an input to cause the implantable medical device to output the alert based a condition of the implantable medical device, and wherein the condition of the implantable medical device is a detected device malfunction comprising one or more of: lead break, memory error, and a communication issue.

Example 35: The method of any combination of examples 19-34, wherein the user interface is configured to receive an input to cause the implantable medical device to output the alert based on a physiological event with the patient, and wherein the detected physiological event comprises one or more of: a gait freeze; a local field potential (LFP) threshold exceeded, a seizure; a bladder fullness, and a missed medication dose.

Example 36: The method of any combination of examples 19-35, wherein the user interface is configured to receive an input to cause the implantable medical device to output the alert based on an action taken by the implantable medical device, and wherein the action taken by the implantable medical device comprises one or more of: a confirmation of a patient input and sending a message to the patient's medical provider.

Example 37: A system includes an external computing device comprising a user interface; an implantable medical device includes a memory configured to store instructions for selecting an alert mode from a plurality of alert modes; and processing circuitry configured to: determine that a condition occurred, the condition associated with at least one of a patient or the implantable medical device; responsive to determining that the condition occurred, select the alert mode from the plurality of alert modes based on the condition and the instructions; and responsive to selecting the alert mode, output, in the selected alert mode, an alert that indicates the condition occurred.

Example 38: The system of example 37, wherein to select an alert mode further depends on the patient's ability to detect one or more alert modes of the plurality of alert modes, wherein the user interface is configured to receive an input regarding the patient ability and provide a recommended alert mode based on the patient ability, and wherein the patient ability comprises a hearing acuity of the patient and a tactile sensitivity of the patient.

Example 39: The system of examples 37 and 38, wherein the user interface is configured to receive an input to cause the implantable medical device to assign a first selected alert mode of the plurality of alert modes to a first detected condition and to assign a second selected alert mode of the plurality of alert modes to a second detected condition.

Example 40: The system of any combination of examples 37-39, wherein the user interface is configured to receive an input to cause the implantable medical device to withhold the alert based on an activity level of the patient.

Example 41: The system of any combination of examples 37-40, wherein the user interface is configured to receive an input to cause the implantable medical device to set a second selected alert mode of the plurality of alert modes as an escalation alert mode.

Example 42: The system of any combination of examples 37-41, wherein the user interface is configured to receive an input to cause the implantable medical device to set a first selected alert mode of the plurality of alert modes as the default alert mode.

Example 43: A system that includes a movement sensor configured to be implanted within a patient and generate a movement signal; and processing circuitry configured to be implanted within the patient and configured to: receive the movement signal from the movement sensor; determine that the movement signal is representative of a communication from the patient; responsive to determining that the movement signal is representative of the communication: output an alert to the patient that is associated with the communication; and perform an action requested by the communication.

Example 44: The system of example 43, further comprising an implantable medical device that comprises the movement sensor and the processing circuitry.

Example 45: The system of examples 43 and 44, further comprising an implantable medical device that comprises a battery, wherein the processing circuitry is configured to perform the action by obtaining a discharge level of the battery, and wherein the alert indicates the discharge level of the battery.

Example 46: The system of any combination of examples 43-45, wherein the communication comprises one or more taps on a housing of the implantable medical device that houses the movement sensor, and wherein the movement sensor is configured to detect the one or more taps as one or more movements in a single direction exceeding a threshold.

Example 47: The system of any combination of examples 43-46, wherein the one or more taps is a plurality of taps, and wherein the processing circuitry is configured to: determine a pattern defined by the plurality of taps, based on the movement signal, determine the communication based on the pattern, and select the action to perform, based on the determined communication.

Example 48: The system of any combination of examples 43-47, wherein the pattern comprises a predetermined number of taps within a predetermined duration.

Example 49: The system of any combination of examples 43-48, wherein the pattern comprises a predetermined frequency of the plurality of taps, and wherein the predetermined frequency comprises a predetermined period of time between at least two taps of the plurality of taps.

Example 50: The system of any combination of examples 43-49, wherein the plurality of taps comprises a first tap, a second tap, and a third tap, wherein the pattern comprises a first period of time between the first tap and the second tap and a second period of time between the second tap and the third tap, and wherein the first period is longer than the second period.

Example 51: The system of any combination of examples 43-50, wherein the plurality of taps comprises a first tap and a second tap, wherein the pattern comprises a first tap at a first magnitude and a second tap at a second magnitude, and wherein the first magnitude is greater than the second magnitude.

Example 52: The system of any combination of examples 43-51, wherein the communication comprises one or more jiggle movements of a housing of an implantable medical device that houses the movement sensor, and wherein the movement sensor is configured to detect the one or more jiggle movements as one or more movements in opposite directions exceeding a threshold.

Example 53: The system of any combination of examples 43-52, wherein the movement sensor comprises accelerometer circuitry.

Example 54: The system of any combination of examples 43-53, further comprising a memory configured to store instructions for selecting an alert mode from a plurality of alert modes, wherein the processing circuitry is configured to output the alert based on the selected alert mode.

Example 55: The system of any combination of examples 43-54, wherein the processing circuitry is further configured to select the alert mode from the plurality of alert modes based on the communication and the instructions in response to determining the movement signal is representative of the communication.

Example 56: The system of any combination of examples 43-55, wherein the processing circuitry is configured to perform the action by changing a stimulation therapy mode, and wherein the alert indicates that the stimulation therapy mode has changed.

Example 57: The system of any combination of examples 43-56, wherein the processing circuitry is configured to change the stimulation therapy mode by at least one of turning on stimulation therapy or turning off stimulation therapy.

Example 58: The system of any combination of examples 43-57, wherein the plurality of alert modes comprises a modification to stimulation therapy delivered by the implantable medical device, wherein the modification to the stimulation therapy comprises one or more of: withhold the stimulation therapy for a predetermined duration; change intensity of the stimulation therapy for the predetermined duration; interleave an alert signal with the stimulation therapy for the predetermined duration.

Example 59: The system of any combination of examples 43-58, wherein the processing circuitry is configured to modify the stimulation therapy in a predetermined pattern.

Example 60: The system of any combination of examples 43-59, wherein responsive to the detected communication the processing circuitry is configured to change a sensing mode and to output an alert indicating that the sensing mode has changed.

Example 61: The system of any combination of examples 43-60, wherein the change stimulation therapy mode is to turn off sensing.

Example 62: The system of any combination of examples 43-61, further comprising an external computing device configured to: receive an input from a user via a user interface, wherein the input comprises the instructions for selecting the alert mode; send the instructions to the implantable medical device.

Example 63: The system of any combination of examples 43-62, wherein the patient ability comprises a hearing acuity of the patient and a tactile sensory sensitivity of the patient.

Example 64: The system of any combination of examples 43-63, wherein the plurality of alert modes comprises one or more of: a vibration of the implantable medical device; an audio sound generated by the implantable medical device; and a communication to an external device.

Example 65: The system of any combination of examples 43-64, wherein the implantable medical device comprises a housing, and wherein the plurality of alert modes comprises housing stimulation, wherein the housing stimulation comprises a stimulation above a perception level of the patient at an implant site of the implantable medical device.

Example 66. The system of any combination of examples 43-65, wherein the housing of the implantable medical device acts as a cathode to deliver the housing stimulation.

Example 67: A method comprising receiving, by processing circuitry configured to be implanted within a patient, a movement signal from a movement sensor, wherein the movement sensor is also configured to be implanted within the patient; determining, by processing circuitry, that the movement signal is representative of a communication from the patient; responsive to determining that the movement signal is representative of the communication: causing, by the processing circuitry, an alert to be output to the patient that is associated with the communication; and performing an action requested by the communication.

Example 68: The method of example 67, wherein an implantable medical device comprises the movement sensor and the processing circuitry.

Example 69: The method of example 67 and 68, wherein the implantable medical device comprises a battery, wherein the processing circuitry is configured to perform the action by obtaining a discharge level of the battery, and wherein the alert indicates the discharge level of the battery.

Example 70: The method of any combination of examples 67-69, wherein the communication comprises one or more taps on a housing of the implantable medical device that houses the movement sensor, and wherein the movement sensor is configured to detect the one or more taps as one or more movements in a single direction exceeding a threshold.

Example 71: The method of any combination of examples 67-70, wherein the one or more taps is a plurality of taps, and wherein the processing circuitry is configured to: determine a pattern defined by the plurality of taps, based on the movement signal, determine the communication based on the pattern, and select the action to perform, based on the determined communication.

Example 72: The method of any combination of examples 67-71, further comprising, receiving, by the processing circuitry of the implantable medical device, instructions from an external computing device for selecting an alert mode from a plurality of alert modes for the alert associated with the communication.

Example 73: The method of any combination of examples 67-72, wherein the movement sensor comprises accelerometer circuitry.

Example 74: The method of any combination of examples 67-73, further includes responsive to determining the movement signal is representative of the communication, retrieving, by the processing circuitry, and from instructions stored at a memory, instructions for selecting an alert mode from a plurality of alert modes, and selecting the alert mode based on the instructions; outputting the alert based on the selected alert mode.

Example 75: The method of any combination of examples 67-74, wherein performing the action comprises changing a stimulation therapy mode, and wherein the alert indicates that the stimulation therapy mode has changed.

Example 76: The method of any combination of examples 67-75, wherein the action requested by the communication comprises changing, by the processing circuitry, a sensing mode and the alert associated with the communication comprises indicating that the sensing mode has changed.

Example 77: A computer-readable medium with instructions for causing a programmable processor of an implantable medical device to: receive a movement signal from a movement sensor, wherein the implantable medical device comprises the movement sensor; determine that the movement signal is representative of a communication from the patient; responsive to determining that the movement signal is representative of the communication: cause an alert to be output to the patient that is associated with the communication; and perform an action requested by the communication.

Example 78: An implantable medical device that includes a memory; stimulation circuitry configured to deliver electrical stimulation to a patient; and processing circuitry operably coupled to the memory and configured to: control the stimulation circuitry to output electrical stimulation therapy to a patient via a first electrode combination; and control the stimulation circuitry to output a notification stimulation via a second electrode combination and interleaved with the electrical stimulation therapy, wherein the notification stimulation comprises an intensity above a perception level of the patient, and wherein the second electrode combination comprises an electrode disposed at an implant site of the implantable medical device.

Example 79: The implantable medical device of example 78, wherein a housing of the implantable medical device comprises the electrode disposed at the implant site.

Example 80: The implantable medical device of examples 78 and 79, wherein the electrode disposed at the implant site acts as a cathode for the notification stimulation delivered by the stimulation circuitry.

Example 81: The implantable medical device of any combination of examples 78-80, wherein an electrode integrated with the housing of the implantable medical device but electrically isolated from the housing acts as a cathode to deliver the notification stimulation.

Example 82: The implantable medical device of any combination of examples 78-81, wherein an electrode on a lead implanted proximal to the implant site acts as a cathode to deliver the notification stimulation.

Example 83: The implantable medical device of any combination of examples 78-82, wherein the second electrode combination comprises one or more electrodes implanted separate from the implant site and configured to act as one or more anodes for the notification stimulation.

Example 84: The implantable medical device of any combination of examples 78-83, wherein the processing circuitry is configured to control the stimulation circuitry to deliver the notification stimulation with a pattern of pulses detectable by the patient.

Example 85: The implantable medical device of any combination of examples 78-84, wherein the processing circuitry is configured to control the stimulation circuitry to deliver the pattern of pulses at a predetermined pulse repetition rate.

Example 86: The implantable medical device of any combination of examples 78-85, wherein the pattern comprises a first period of time between a first pulse and a second pulse of the plurality of pulses and a second period of time between the second pulse and a third pulse, and wherein the first period is longer than the second period.

Example 87: The implantable medical device of any combination of examples 78-86, wherein the pulses detectable by the patient comprise a first pulse at a first magnitude and a second pulse at a second magnitude, and wherein the first magnitude is greater than the second magnitude.

Example 88: The implantable medical device of any combination of examples 78-87, wherein the pulses detectable by the patient comprise a gradually increasing magnitude for each pulse of the plurality of pulses over a predetermined duration.

Example 89: The implantable medical device of any combination of examples 78-88, wherein the electrical stimulation therapy comprises spinal cord stimulation, and wherein the first electrode combination comprises one or more electrodes configured to be implanted adjacent the spinal cord.

Example 90: The implantable medical device of any combination of examples 78-89, wherein the electrical stimulation therapy comprises tibial therapy stimulation, and wherein the first electrode combination comprises one or more electrodes configured to be implanted adjacent to a tibial nerve.

Example 91: A method comprising controlling, by processing circuitry operably coupled to a memory, stimulation circuitry configured to output electrical stimulation therapy to a patient; and controlling, by the processing circuitry, the stimulation circuitry to output the electrical stimulation therapy to a patient via a first electrode combination; and controlling, by the processing circuitry, the stimulation circuitry to output a notification stimulation interleaved with the electrical stimulation therapy wherein the notification stimulation comprises an intensity above a perception level of the patient, and wherein the second electrode combination comprises an electrode disposed at an implant site of the implantable medical device.

Example 92: The method of example 91, wherein a housing of the implantable medical device comprises the electrode disposed at the implant site.

Example 93: The method of examples 91 and 92, wherein the electrode disposed at the implant site acts as a cathode for the notification stimulation delivered by the stimulation circuitry.

Example 94: The method of any combination of examples 91-93, wherein an electrode on a lead implanted proximal to the implant site acts as a cathode to deliver the notification stimulation.

Example 95: The method of any combination of examples 78-94, wherein the processing circuitry is configured to control the stimulation circuitry to deliver the notification stimulation with a pattern of pulses detectable by the patient.

Example 96: The method of any combination of examples 78-95, wherein the pulses detectable by the patient comprise a first pulse at a first magnitude and a second pulse at a second magnitude, and wherein the first magnitude is greater than the second magnitude.

Example 97: The method of any combination of examples 78-96, wherein the electrical stimulation therapy comprises spinal cord stimulation, and wherein the first electrode combination comprises one or more electrodes configured to be implanted adjacent the spinal cord.

Example 98: A computer-readable medium comprising instructions for causing a programmable processor of a medical device to control stimulation circuitry, wherein the stimulation circuitry is configured to: output electrical stimulation therapy to a patient; and output a notification stimulation interleaved with the electrical stimulation therapy wherein the notification stimulation comprises a housing stimulation at an implant site of the implantable medical device above a perception level of the patient.

Various examples of the disclosure have been described. These and other examples are within the scope of the following claims.

What is claimed is:
1. An implantable medical device comprising:
a memory;
stimulation circuitry configured to deliver electrical stimulation to a patient; and
processing circuitry operably coupled to the memory and configured to:

control the stimulation circuitry to output electrical stimulation therapy to a patient via a first electrode combination, wherein the electrical stimulation therapy comprises a first plurality of pulses, wherein the first plurality of pulses are output at a pulse rate; and control the stimulation circuitry to output a notification stimulation defined by a predetermined pattern of a second plurality of pulses via a second electrode combination, wherein the second plurality of pulses are interleaved with at least some pulses of the first plurality of pulses of the electrical stimulation therapy to maintain the predetermined pattern of the second plurality of pulses, wherein the notification stimulation comprises an intensity above a perception level of the patient, wherein the notification stimulation comprises an acknowledgement notification to a communication from the patient, and wherein the second electrode combination comprises an electrode disposed at an implant site of the implantable medical device.

2. The implantable medical device of claim 1,
wherein a housing of the implantable medical device comprises the electrode disposed at the implant site, and wherein the electrode disposed at the implant site acts as a cathode for the notification stimulation delivered by the stimulation circuitry.

3. The implantable medical device of claim 1, wherein the notification stimulation comprises a change in stimulation that causes a side effect perceptible to the patient.

4. The implantable medical device of claim 1, wherein an electrode integrated with the housing of the implantable medical device but electrically isolated from the housing acts as a cathode to deliver the notification stimulation.

5. The implantable medical device of claim 1, wherein an electrode on a lead implanted proximal to the implant site acts as a cathode to deliver the notification stimulation.

6. The implantable medical device of claim 1, wherein the second electrode combination comprises one or more electrodes implanted separate from the implant site and configured to act as one or more anodes for the notification stimulation.

7. The implantable medical device of claim 1, wherein the second plurality of pulses is detectable by the patient as the notification stimulation.

8. The implantable medical device of claim 7, wherein the processing circuitry is configured to control the stimulation circuitry to deliver the second plurality of pulses at a predetermined pulse repetition rate.

9. The implantable medical device of claim 7,
wherein the second plurality of pulses comprises a first period of time between a first pulse and a second pulse of a plurality of pulses and a second period of time between the second pulse and a third pulse, and
wherein the first period is longer than the second period.

10. The implantable medical device of claim 7,
wherein the second plurality of pulses detectable by the patient comprise a first pulse at a first magnitude and a second pulse at a second magnitude, and
wherein the first magnitude is greater than the second magnitude.

11. The implantable medical device of claim 7, wherein the second plurality of pulses detectable by the patient comprise a gradually increasing magnitude for each pulse of the second plurality of pulses over a predetermined duration.

12. The implantable medical device of claim 1, wherein the electrical stimulation therapy comprises spinal cord stimulation, and wherein the first electrode combination comprises one or more electrodes configured to be implanted adjacent the spinal cord.

13. The implantable medical device of claim 1, wherein the electrical stimulation therapy comprises tibial therapy stimulation, and wherein the first electrode combination comprises one or more electrodes configured to be implanted adjacent to a tibial nerve.

14. A method comprising:
controlling, by processing circuitry operably coupled to a memory, stimulation circuitry configured to output electrical stimulation therapy to a patient; and controlling, by the processing circuitry, the stimulation circuitry to output the electrical stimulation therapy to a patient via a first electrode combination, wherein the electrical stimulation therapy comprises a first plurality of pulses, wherein the first plurality of pulses are output at a pulse rate; and controlling, by the processing circuitry, the stimulation circuitry to output a notification stimulation defined by a predetermined pattern of a second plurality of pulses, wherein the second plurality of pulses are interleaved with at least some of the first plurality of pulses of the electrical stimulation therapy to maintain the predetermined pattern of the second plurality of pulses via a second electrode combination, wherein the notification stimulation comprises an intensity above a perception level of the patient, wherein the notification stimulation comprises an acknowledgement notification to a communication from the patient, and wherein the second electrode combination comprises an electrode disposed at an implant site of the implantable medical device.

15. The method of claim 14, wherein a housing of the implantable medical device comprises the electrode disposed at the implant site.

16. The method of claim 14, wherein the electrode disposed at the implant site acts as a cathode for the notification stimulation delivered by the stimulation circuitry.

17. The method of claim 14, wherein an electrode on a lead implanted proximal to the implant site acts as a cathode to deliver the notification stimulation.

18. The method of claim 14, wherein the second plurality of pulses is detectable by the patient as the notification stimulation.

19. The method of claim 18,
wherein the second plurality of pulses detectable by the patient comprise a first pulse at a first magnitude and a second pulse at a second magnitude, and
wherein the first magnitude is greater than the second magnitude.

20. The method of claim 14, wherein the electrical stimulation therapy comprises spinal cord stimulation, and wherein the first electrode combination comprises one or more electrodes configured to be implanted adjacent the spinal cord.

21. A non-transitory computer-readable storage medium comprising instructions for causing a programmable processor of a medical device to control stimulation circuitry, wherein the stimulation circuitry is configured to:
output electrical stimulation therapy to a patient, wherein the electrical stimulation therapy comprises a first plurality of pulses, wherein the first plurality of pulses are output at a pulse rate; and output a notification stimulation defined by a predetermined pattern of a second plurality of pulses, wherein the second plurality of pulses are interleaved with at least some of the first plurality of pulses of the electrical stimulation therapy to maintain the predetermined pattern of the second plurality of pulses, wherein the notification stimulation comprises a housing stimulation at an implant site of the implantable medical device, wherein the housing stimulation comprises stimulation above a perception level of the patient, and wherein the notification stimulation comprises an acknowledgement notification to a communication from the patient.

* * * * *